US009186212B2

(12) United States Patent
Nabutovsky et al.

(10) Patent No.: US 9,186,212 B2
(45) Date of Patent: Nov. 17, 2015

(54) FEEDBACK SYSTEMS AND METHODS UTILIZING TWO OR MORE SITES ALONG DENERVATION CATHETER

(71) Applicant: St. Jude Medical, Cardiology Division, Inc., St. Paul, MN (US)

(72) Inventors: Yelena Nabutovsky, Sunnyvale, CA (US); Edward Karst, Los Angeles, CA (US); Xiaoyi Min, Thousand Oaks, CA (US); Stuart Rosenberg, Castaic, CA (US); Kritika Gupta, Sunnyvale, CA (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 321 days.

(21) Appl. No.: 13/840,244

(22) Filed: Mar. 15, 2013

(65) Prior Publication Data

US 2014/0276746 A1    Sep. 18, 2014

(51) Int. Cl.
| *A61B 18/00* | (2006.01) |
| *A61B 18/14* | (2006.01) |
| *A61B 5/053* | (2006.01) |
| *A61B 5/00* | (2006.01) |

(Continued)

(52) U.S. Cl.
CPC ........... *A61B 18/1492* (2013.01); *A61B 5/0538* (2013.01); *A61B 5/4848* (2013.01); *A61B 5/0261* (2013.01); *A61B 5/201* (2013.01); *A61B 8/06* (2013.01); *A61B 2018/00863* (2013.01)

(58) Field of Classification Search
CPC ............... A61B 18/14; A61B 2018/00577; A61B 2018/00511; A61B 18/1492; A61B 5/0538; A61B 5/4848; A61B 8/06

USPC ................................................... 606/32, 41, 42
See application file for complete search history.

(56) References Cited

U.S. PATENT DOCUMENTS

| 3,650,277 A | 3/1972 | Sjostrand et al. |
| 4,658,819 A | 4/1987 | Harris et al. |

(Continued)

FOREIGN PATENT DOCUMENTS

| WO | 97/45157 | 12/1997 |
| WO | 00/66020 | 11/2000 |

(Continued)

OTHER PUBLICATIONS

Millard, F.C. et al, Renal Embolization for Ablation of Function in Renal Failure and Hypertension, Postgraduate Medical Journal (1989) 65, 729-734.

(Continued)

*Primary Examiner* — Christopher D Koharski
*Assistant Examiner* — Michael Carey
(74) *Attorney, Agent, or Firm* — Armstrong Teasdale LLP

(57) ABSTRACT

A renal denervation system includes a renal denervation catheter and a flow determining system. The renal denervation catheter includes a plurality of ablation members positioned at a distal end portion thereof. The renal denervation catheter is insertable into a renal artery. The flow determining system includes a processor and first and second flow determining members spaced apart on the renal denervation catheter. The processor is configured to determine a change in blood flow through the renal artery resulting from a renal denervation procedure using the renal denervation catheter in response to input from the first and second flow determining members.

6 Claims, 12 Drawing Sheets

(51) Int. Cl.
  *A61B 8/06*   (2006.01)
  *A61B 5/026*  (2006.01)
  *A61B 5/20*   (2006.01)

(56) References Cited

U.S. PATENT DOCUMENTS

| | | | |
|---|---|---|---|
| 5,035,694 | A | 7/1991 | Kasprzyk et al. |
| 5,255,679 | A | 10/1993 | Imran |
| 5,300,068 | A | 4/1994 | Rosar et al. |
| 5,368,591 | A | 11/1994 | Lennox et al. |
| 5,387,233 | A | 2/1995 | Alferness et al. |
| 5,465,717 | A | 11/1995 | Imran et al. |
| 5,531,779 | A | 7/1996 | Dahl et al. |
| 5,598,848 | A | 2/1997 | Swanson et al. |
| 5,607,462 | A | 3/1997 | Imran |
| 5,628,313 | A | 5/1997 | Webster, Jr. |
| 5,676,662 | A | 10/1997 | Fleischhacker et al. |
| 5,707,400 | A | 1/1998 | Terry, Jr. et al. |
| 5,769,077 | A | 6/1998 | Lindegren |
| 5,772,590 | A | 6/1998 | Webster, Jr. |
| 5,893,885 | A | 4/1999 | Webster, Jr. |
| 5,897,553 | A | 4/1999 | Mulier et al. |
| 5,954,649 | A | 9/1999 | Chia et al. |
| 5,954,719 | A | 9/1999 | Chen et al. |
| 6,004,269 | A | 12/1999 | Crowley et al. |
| 6,012,457 | A | 1/2000 | Lesh |
| 6,016,437 | A | 1/2000 | Tu et al. |
| 6,024,740 | A | 2/2000 | Lesh et al. |
| 6,073,048 | A | 6/2000 | Kieval et al. |
| 6,096,037 | A | 8/2000 | Mulier et al. |
| 6,117,101 | A | 9/2000 | Diederich et al. |
| 6,161,543 | A | 12/2000 | Cox et al. |
| 6,178,349 | B1 | 1/2001 | Kieval |
| 6,200,312 | B1 | 3/2001 | Zikorus et al. |
| 6,216,044 | B1 | 4/2001 | Kordis |
| 6,233,491 | B1 | 5/2001 | Kordis et al. |
| 6,283,951 | B1 | 9/2001 | Flaherty et al. |
| 6,287,608 | B1 | 9/2001 | Levin et al. |
| 6,292,695 | B1 | 9/2001 | Webster, Jr. et al. |
| 6,322,559 | B1 | 11/2001 | Daulton et al. |
| 6,460,545 | B2 | 10/2002 | Kordis |
| 6,522,926 | B1 | 2/2003 | Kieval et al. |
| 6,613,045 | B1 | 9/2003 | Laufer et al. |
| 6,616,624 | B1 | 9/2003 | Kieval |
| 6,635,054 | B2 | 10/2003 | Fjield et al. |
| 6,656,174 | B1 | 12/2003 | Hegde et al. |
| 6,669,655 | B1 | 12/2003 | Acker et al. |
| 6,699,231 | B1 | 3/2004 | Sterman et al. |
| 6,748,255 | B2 | 6/2004 | Fuimaono et al. |
| 6,805,131 | B2 | 10/2004 | Kordis |
| 6,845,267 | B2 | 1/2005 | Harrison et al. |
| 6,954,977 | B2 | 10/2005 | Maguire et al. |
| 6,970,730 | B2 | 11/2005 | Fuimaono et al. |
| 7,122,031 | B2 | 10/2006 | Edwards et al. |
| 7,149,574 | B2 | 12/2006 | Yun et al. |
| 7,155,284 | B1 | 12/2006 | Whitehurst et al. |
| 7,162,303 | B2 | 1/2007 | Levin et al. |
| 7,245,955 | B2 | 7/2007 | Rashidi |
| 7,291,146 | B2 | 11/2007 | Steinke et al. |
| 7,363,076 | B2 | 4/2008 | Yun et al. |
| 7,419,486 | B2 | 9/2008 | Kampa |
| 7,465,288 | B2 | 12/2008 | Dudney et al. |
| 7,468,062 | B2 | 12/2008 | Oral et al. |
| 7,481,803 | B2 | 1/2009 | Kesten et al. |
| 7,653,438 | B2 | 1/2010 | Deem et al. |
| 7,717,948 | B2 | 5/2010 | Demarais et al. |
| 7,742,795 | B2 | 6/2010 | Stone et al. |
| 7,850,685 | B2 | 12/2010 | Kunis et al. |
| 7,949,407 | B2 | 5/2011 | Kaplan et al. |
| 8,145,316 | B2 | 3/2012 | Deem et al. |
| 8,224,416 | B2 | 7/2012 | de la Rama et al. |
| 8,343,213 | B2 | 1/2013 | Salahieh et al. |
| 8,347,891 | B2 | 1/2013 | Demarais et al. |
| 8,442,639 | B2 | 5/2013 | Walker et al. |
| 8,454,594 | B2 | 6/2013 | Demarais et al. |
| 8,545,495 | B2 | 10/2013 | Scheib |
| 9,022,948 | B2 | 5/2015 | Wang |
| 2002/0068885 | A1 | 6/2002 | Harhen et al. |
| 2002/0120304 | A1 | 8/2002 | Mest |
| 2002/0123749 | A1 | 9/2002 | Jain |
| 2003/0050681 | A1 | 3/2003 | Pianca et al. |
| 2003/0060858 | A1 | 3/2003 | Kieval et al. |
| 2003/0074039 | A1 | 4/2003 | Puskas |
| 2003/0114739 | A1 | 6/2003 | Fuimaono et al. |
| 2003/0216792 | A1 | 11/2003 | Levin et al. |
| 2003/0233099 | A1 | 12/2003 | Danaek et al. |
| 2004/0215186 | A1 | 10/2004 | Cornelius et al. |
| 2005/0288730 | A1 | 12/2005 | Deem et al. |
| 2006/0089678 | A1 | 4/2006 | Shalev |
| 2007/0135875 | A1 | 6/2007 | Demarais et al. |
| 2008/0255478 | A1 | 10/2008 | Burdette |
| 2009/0076409 | A1 | 3/2009 | Wu et al. |
| 2009/0234231 | A1 | 9/2009 | Knight et al. |
| 2010/0016762 | A1 | 1/2010 | Thapliyal et al. |
| 2010/0094209 | A1 | 4/2010 | Drasler et al. |
| 2010/0168737 | A1 | 7/2010 | Grunewald |
| 2010/0249773 | A1 | 9/2010 | Clark et al. |
| 2010/0268307 | A1 | 10/2010 | Demarais et al. |
| 2010/0286684 | A1 | 11/2010 | Hata et al. |
| 2011/0004087 | A1 | 1/2011 | Fish et al. |
| 2011/0118726 | A1 | 5/2011 | de la Rama et al. |
| 2011/0137298 | A1 | 6/2011 | Nguyen et al. |
| 2011/0160720 | A1 | 6/2011 | Johnson |
| 2011/0213231 | A1 | 9/2011 | Hall et al. |
| 2011/0257641 | A1 | 10/2011 | Hastings et al. |
| 2011/0264011 | A1 | 10/2011 | Wu et al. |
| 2011/0264086 | A1 | 10/2011 | Ingle |
| 2012/0143097 | A1 | 6/2012 | Pike, Jr. |
| 2012/0143298 | A1 | 6/2012 | Just et al. |
| 2012/0150049 | A1 | 6/2012 | Zielinski |
| 2012/0232409 | A1* | 9/2012 | Stahmann |
| 2012/0296232 | A1 | 11/2012 | Ng |
| 2012/0323233 | A1 | 12/2012 | Maguire et al. |
| 2013/0116737 | A1 | 5/2013 | Edwards et al. |
| 2013/0131743 | A1 | 5/2013 | Yamasaki et al. |
| 2013/0144251 | A1 | 6/2013 | Sobotka |
| 2013/0172715 | A1 | 7/2013 | Just et al. |

FOREIGN PATENT DOCUMENTS

| | | |
|---|---|---|
| WO | 01/00273 | 1/2001 |
| WO | 01/22897 | 4/2001 |
| WO | 02/26314 | 4/2002 |
| WO | 03/082080 | 10/2003 |
| WO | 2006/041881 | 4/2006 |
| WO | 2007/149970 | 12/2007 |
| WO | 2008/141150 | 11/2008 |
| WO | 2008/151001 | 12/2008 |
| WO | 2012/064818 | 5/2012 |
| WO | 2012/106492 | 8/2012 |
| WO | 2014/007871 | 1/2014 |

OTHER PUBLICATIONS

Moak, Jeffrey P. et al, Case Report: Pulmonary Vein Stenosis Following RF Ablation of Paroxysmal Atrial Fibrillation: Successful Treatment with Balloon Dilation, Journal of Interventional Cardiac Electrophysiology, Dec. 2000, 4, 4:621-631.

Mogil, Robert A. et al, Renal Innervation and Renin Activity in Salt Metabolism and Hypertension, American Journal of Physiology, vol. 216, No. 4, Apr. 1969, 693-697.

Morita, Hironobu et al, Neural Control of Urinary Sodium Excretion During Hypertonic NaCl Load in Conscious Rabbits: Role of Renal and Hepatic Nerves and Baroreceptors, Journal of the Autonomic Nervous System, 34 (1991) 157-170.

Morrissey, D.M. et al, Sympathectomy in the Treatment of Hypertension, The Lancet, Feb. 1953, 403-408.

Mortara, Andrea et al, Nonselective Beta-Adrenergic Blocking Agent, Carvedilol, Improves Arterial Baroflex Gain and Heart Rate Variability in Patients With Stable Chronic Heart Failure, Journal of the American College of Cardiology, vol. 36, No. 5, 2000, 1612-1618.

(56) References Cited

OTHER PUBLICATIONS

Moss, Jonathan, Interventional Radiology and Renal Denervation, Interventions, vol. 13, Issue 3, 2013.
Naghavi, Morteza et al, Thermography Basket Catheter: In Vivo Measurement of the Temperature of Atherosclerotic Plaques for Detection of Vulnerable Plaques, Catheterization and Cardiovascular Interventions 59:52-59 (2003).
Naidoo, N. et al, Thoracic Splanchnic Nerves: Implications for Splanchnic Denervation, Journal of Anatomy, Nov. 2001;199(Pt 5):585-590.
Nakagawa, A. et al, Selective Ablation of Porcine and Rabbit Liver Tissue Using Radiofrequency: Preclinical Study, European Surgical Research, 1999;31:371-379.
Nakagawa, Hiroshi et al, Inverse Relationship Between Electrode Size and Lesion Size During Radiofrequency Ablation With Active Electrode Cooling, Circulation. Aug. 4, 1998;98(5):458-465.
Nanni, Gregg S. et al, Control of Hypertension by Ethanol Renal Ablation, Radiology 148: 51-54, Jul. 1983.
Ndegwa, S., Catheter-Based Renal Denervation for Treatment-Resistant Hypertension [Issues in emerging health technologies issue 121]. Ottawa: Canadian Agency for Drugs and Technologies in Health; 2013.
Neutel, Joel M., Hypertension and Its Management: A Problem in Need of New Treatment Strategies, Journal of Renin-Angiotensin-Aldosterone System 2000 1: S10-S13.
Newcombe, C.P. et al, Sympathectomy for Hypertension, British Medical Journal, Jan. 1959, 142-144.
Ng, Fu Siong et al, Catheter Ablation of Atrial Fibrillation, Clinical Cardiology, 25, 384-394 (2002).
Norman, Roger A. et al, Role of the Renal Nerves in One-Kidney, One Clip Hypertension in Rats, Hypertension Journal of The American Heart Association, 1984;6:622-626.
Nozawa, Takashi et al, Effects of Long-Term Renal Sympathetic Denervation on Heart Failure After Myocardial Infarction in Rats, Heart Vessels (2002) 16:51-56.
O'Connor, Brian K. et al, Radiofrequency Ablation of a Posteroseptal Accessory Pathway Via the Middle Cardiac Vein in a Six-Year-Old Child, PACE, vol. 20, Oct. 1997, Part 1, 2504-2507.
O'Hagen, Kathleen P. et al, Renal Denervation Decreases Blood Pressure in DOCA-Treated Miniature Swine With Established Hypertension, American Journal of Hypertension, 1990; 3:62-64.
Oliveira, Vera L.L. et al, Renal Denervation Normalizes Pressure and Baroreceptor Reflex in High Renin Hypertension in Conscious Rats, Hypertension vol. 19, No. 2 Feb. 1992, Supplement II, II-17-II-21.
Omran, Heyder et al, Echocardiographic Imaging of Coronary Sinus Diverticula and Middle Cardiac Veins in Patients with Preexcitation Syndrome: Impact—on Radiofrequency Catheter Ablation of Posteroseptal Accessory Pathways, PACE, vol. 18, Jun. 1995, 1236-1243.
Oparil, Suzanne et al, Renal Nerve Ablation: Emerging Role in Therapeutics; Blood Pressure, Oct. 2011, vol. 20, No. 5, pp. 253-255.
Oral, Hakan et al, Pulmonary Vein Isolation for Paroxysmal and Persistent Atrial Fibrillation, Circulation Journal of The American Heart Association, 2002;105:1077-1081.
Osborn, Jeffrey L. et al, Long-Term Increases in Renal Sympathetic Nerve Activity and Hypertension, Clinical and Experimental Pharmacology and Physiology (1997) 24,72-76.
Osborn, John W., The Sympathetic Nervous System and Long-Term Regulation of Arterial Pressure: What Are the Critical Questions?, Clinical and Experimental Pharmacology and Physiology (1997) 24, 68-71.
Ou, Baiqing et al, Baroreflex Sensitivity Predicts the Induction of Ventricular Arrhythmias by Cesium Chloride in Rabbits, Japanese Circulation Journal, 1999; 63: 783-788.
Oz, Mehmet, Pressure Relief, Time Magazine, Monday, Jan. 9, 2012.
Page, Irvine H. et al, Mechanisms, Diagnosis and Treatment of Hypertension of Renal Vascular Origin, Annal of Internal Medicine, Aug. 1959, vol. 51, No. 2, 196-211.

Page, Irvine H. et al, Mechanisms, Diagnosis and Treatment of Hypertension of Renal Vascular Origin; Annals of Internal Medicine, Aug. 1959;51:196-211.
Page, Irvine H. et al, The Effect of Renal Denervation on the Level of Arterial Blood Pressure and Renal Function in Essential Hypertension, Journal of Clinical Investigation, 1935;14(1):27-30.
Page, Irvine H. et al, The Effects of Renal Denervation on Patients Suffering from Nephritis, J Clin Invest. 1935;14(4):443-458.
Page, Irvine H., The Effect of Renal Efficiency of Lowering Arterial Blood Pressure in Cases of Essential Hypertension and Nephritis, Journal of Clinical Investigation, Nov. 1934; 13(6): 909-915.
Page, Max, Section of Surgery, Discussion on the Surgical Treatment of Hypertension, Proceedings of the Royal Society of Medicine, vol. XLI, Feb. 1948, 359-372.
Papademetriou, Vasilios, Hypertension and the Simplicity Renal Denervation System, Scientific Background, www.medtronic.com, 2011.
Pappone, Carlo et al, Circumferential Radiofrequency Ablation of Pulmonary Vein Ostia: A New Anatomic Approach for Curing Atrial Fibrillation, Circulation, Journal of The American Heart Association, 2000;102:2619-2628.
Parati, Gianfranco et al, The Human Sympathetic Nervous System: Its Relevance in Hypertension and Heart Failure, European Heart Journal (2012) 33, 1058-1066.
Parmar, Arundhati, Analyst: Medtronic Will Likely Acquire Another Hypertension Therapy Firm, Medcity News, Apr. 27, 2012; 3:06 p.m.; medcitynews.com.
Pavlovich, Christian P. et al, Percutaneous Radio Requency Ablation of Small Renal Tumors: Initial Results; The Journal of Urology, vol. 167, 10-15, Jan. 2002.
Pearce, John A. et al, Blood Vessel Architectural Features and Their Effect on Thermal Phenomena, Critical Reviews, vol. CR75, Bellingham, WA: SPIE Optical Engineering Press; 2000, p. 231-277.
Peet, Max Minor, Hypertension and Its Surgical Treatment by Bilateral Supradiaphragmatic Splanchnicectomy, American Journal of Surgery, vol. 75, Issue 1, Jan. 1948, 48-68.
Perry, C. Bruce, Malignant Hypertension Cured by Unilateral Nephrectomy, British Heart Journal, Jul. 1945; 7(3): 139-142.
Persu, Alexandre et al, Renal Denervation: Ultima Ratio or Standard in Treatment-Resistant Hypertension, Hypertension Journal of The American Heart Association, Sep. 2012;60(3):596-606.
Peterson, Helen Hogh et al, Lesion Dimensions During Temperature-Controlled Radiofrequency Catheter Ablation of Left Ventricular Porcine Myocardium Impact of Ablation Site, Electrode Size, and Convective Cooling, Circulation Journal of The American Heart Association, 1999;99:319-325.
Plouin, Pierre-Francois et al, Blood Pressure Outcome of Angioplasty in Atherosclerotic Renal Artery Stenosis A Randomized Trial, Hypertension Journal of The American Heart Association, 1998;31:823-829.
Poutasse, Eugene F., Surgical Treatment of Renal Hypertension, American Journal of Surgery, vol. 107, Jan. 1964, 97-103.
Pugsley, M.K. et al, The Vascular System An Overview of Structure and Function, Journal of Pharmacological and Toxicological Methods 44 (2000) 333-340.
Putney, John Paul, Are Secondary Considerations Still "Secondary"?: An Examination of Objective Indicia of Nonobviousness Five Years After KSR, Intellectual Property Brief, vol. 4, Issue 2, Article 5, 2012, 45-59.
Ramsay, Lawrence E. et al, Blood Pressure Response to Percutaneous Transluminal Angioplasty for Renovascular Hypertension: An Overview of Published Series; British Medical Journal Mar. 3, 1990; 300(6724): 569-572.
Rippy, Marian K. et al, Catheter-Based Renal Sympathetic Denervation: Chronic Preclinical Evidence for Renal Artery Safety, Clin Res Cardiol (2011) 100:1095-1101.
Goyal, R. N., et al., Nanogold Based Electrochemical Sensor for Determination of Norepinephrine in Biological Fluids, Sensor and Actuators B: Chemical, 153(1): p. 232-238, 2011 (7 pp.).
Jin, G., et al., The Electrochemical Modification of Clenbuterol for Biosensors of Dopamine, Norepinephrine, Adrenalin, Ascorbic Acid and Uric Acid at Parrafin-Impregnated Graphite Electrode, Biosensors and Bioelectronics, 24(4): 1031-1035, 2008 (5 pp.).

(56) References Cited

OTHER PUBLICATIONS

Ebert, B. et al., Cyanine Dyes as Contrast Agents for Near-Infrared Imaging in vivo: Acute Tolerance, Pharmacokinetics, and Fluorescence Imaging, Journal of Biomedical Optics, vol. 16(6):066003, Jun. 2011 (10 pp.).
International Search Report and Written Opinion for Application No. PCT/US2014/019488 mailed Sep. 24, 2014.
Abboud, Francois M., The Sympathetic System in Hypertension, State-of-the-Art Review, Hypertension Journal of the American Heart Association, Hypertension 4 (suppl II): II-208-II-225, 1982.
Allen, Edgar V., Sympathectomy for Essential Hypertension, Circulation Journal of the American Heart Association, vol. VI, Jul. 1952, 131-140.
Anderson, Erling A. et al, Elevated Sympathetic Nerve Activity in Borderline Hypertensive Humans, Evidence From Direct Intraneural Recordings, Hypertension Journal of the American Heart Association, vol. 14, No. 2, Aug. 1989, 177-183.
Ardian, Inc., Ardian(R) Receives 2010 EuroPCR Innovation Award and Demonstrates Further Durability of Renal Denervation Treatment for Hypertension, PR Newswire, Jun. 3, 2010.
Arentz, Thomas et al, Feasibility and Safety of Pulmonary Vein Isolation Using a New Mapping and Navigation System in Patients with Refractory Atrial Fibrillation, Circulation Journal of the American Heart Association, Nov. 18, 2003, 2484-2490.
Badoer, Emilio et al, Cardiac Afferents Play the Dominant Role in Renal Nerve Inhibition Elicited by Volume Expansion in the Rabbit, American Journal of Physiology, 1998, R383-R388.
Bakris, George L. et al, Baroreflex Activation Therapy Provides Durable Benefit in Patients with Resistant Hypertension: Results of Long-Term Follow-up in the Rheos Pivotal Trial, J Am Soc Hypertens. Mar.-Apr. 2012;6(2):152-8.
Bao, Gang et al, Blood Pressure Response to Chronic Episodic Hypoxia: Role of the Sympathetic Nervous System, American Journal of Physiology, 1997, 95-101.
Barajas, Luciano et al, Anatomy of the Renal Innervation: Intrarenal Aspects and Ganglia of Origin, Canadian Journal of Physiology and Pharmacology, vol. 70, No. 5, May 1992, 735-749.
Barajas, Luciano et al, Monoaminergic Innervation of the Rat Kidney: A Quantitative Study, American Journal of Physiology, vol. 259, No. 3, Sep. 1990, F503-F511.
Bardram, Linda et al, Late Results After Surgical Treatment of Renovascular Hypertension, A Follow-up Study of 122 Patients 2-18 Years After Surgery, Annals of Surgery, vol. 201, No. 2, Feb. 1985, 219-224.
Bello-Reuss, Elsa et al, Effect of Renal Sympathetic Nerve Stimulation on Proximal Water and Sodium Reabsorption, The Journal of Clinical Investigation, vol. 57, Apr. 1976, 1104-1107.
Bello-Reuss, Elsa et al, Effects of Acute Unilateral Renal Denervation in the Rat, The Journal of Clinical Investigation, vol. 56, Jul. 1975, 208-217.
Benito, Fernando et al, Radiofrequency Catheter Ablation of Accessory Pathways in Infants, Heart, 1997, 78, 160-162.
Bernardi, Luciano et al, Influence of Type of Surgery on the Occurrence of Parasympathetic Reinnervation After Cardiac Transplantation, Circulation Journal of the American Heart Association, Apr. 14, 1998;97(14):1368-74.
Bertog, Stefan C. et al, Renal Denervation for Hypertension, JACC: Cardiovascular Interventions, vol. 5, No. 3, Mar. 2012, 249-258.
Bertram, Harald et al, Coronary Artery Stenosis After Radiofrequency Catheter Ablation of Accessory Atrioventricular Pathways in Children with Ebstein's Malformation, Circulation Journal of the American Heart Association, 2001, 538-543.
Blankestijn, Peter J. et al, Renal Denervation: Potential Impact on Hypertension in Kidney Disease?, Nephrol Dial Transplant (2011) 0: 1-3.
Blankestijn, Peter J. et al, Sympathetic Overactivity in Renal Failure Controlled by ACE Inhibition: Clinical Significance, Nephrol Dial Transplant, 2000, 15, 755-758.

Blum, Ulrich et al, Treatment of Ostial Renal-Artery Stenoses with Vascular Endoprostheses After Unsuccessful Balloon Angioplasty, The New England Journal of Medicine, vol. 336, No. 7, Feb. 1997, 459-465.
Brinkmann, Julia et al, Catheter-Based Renal Nerve Ablation and Centrally Generated Sympathetic Activity in Difficult-to-Control Hypertensive Patients Prospective Case Series, Hypertension. 2012;60:1485-1490.
Brookes, Linda et al, Renal Denervation: Is Reality Meeting Expectations?, An Interview with Michel Azizi, MD, PhD, Medscape, Jan. 7, 2013.
Bunte, Matthew C. et al, Endovascular Treatment of Resistant and Uncontrolled Hypertension, JACC: Cardiovascular Interventions, vol. 6, No. 1, 2013, 1-9.
Calleary, Hickey D. et al, Pre-Transplant Bilateral Native Nephrectomy for Medically Refractory Hypertension, The Irish Medical Journal, Jul.-Aug. 2001;94(7):214-6.
Callens, David J. et al, Narrowing of the Superior Vena Cava-Right Atrium Junction During Radiofrequency Catheter Ablation for Inappropriate Sinus Tachycardia: Analysis with Intracardiac Echocardiography, Journal of the American College of Cardiology, vol. 33, No. 6, 1999, 1667-1670.
Campese, V.M., Is Hypertension in Chronic Renal Failure Neurogenic in Nature?, Nephrol Dial Transplant, 1994, 9: 741-742.
Campese, Vito M. et al, Neurogenic Factors in Renal Hypertension, Current Hypertension Reports, 2002 4: 256-260.
Campese, Vito M. et al, Renal Afferent Denervation Prevents Hypertension in Rats With Chronic Renal Failure, Hypertension, 1995, 25, 878-882.
Campese, Vito M. et al, Renal Afferent Denervation Prevents the Progression of Renal Disease in the Renal Ablation Model of Chronic Renal Failure in Rat, American Journal of Kidney Disease, vol. 26, No. 5, Nov. 1995, 861-865.
Campese, Vito M., Interventional Hypertension: A New Hope or a New Hype? The Need to Redefine Resistant Hypertension, J Hypertens. Nov. 2013;31(11):2118-21.
Canadian Agency for Drugs and Technologies in Health, Catheter-Based Renal Denervation for Treatment-Resistant Hypertension; Issues in Emerging Health Technologies, Issue 121, Mar. 2013.
Carlstedt, Thomas et al, Regrowth of Lesioned Dorsal Root Nerve Fibers into the Spinal Cord of Neonatal Rats, Neuroscience Letters Feb. 10, 1987;74(1):14-8.
Chabanier, H. et al, On the Decapsulation and Neurectomy of the Kidney in Permanent Hypertensive States, The Medical Press, Feb. 22, 1936, No. 16, 307-310.
Ciccone, C D et al, Effects of Acute Renal Denervation on Kidney Function in Deoxycorticosterone Acetate-Hypertensive Swine, Hypertension Journal of the American Heart Association, Oct. 1986, vol. 8, No. 10, 925-931.
Ciriello, John et al, Renal Afferents and Hypertension, Current Hypertension Reports 2002, 4:136-142.
Converse, Richard L. et al, Sympathetic Overactivity in Patients with Chronic Renal Failure, The New England Journal of Medicine, vol. 327, No. 27, 1992, 1912-1918.
Crile, George, The Clinical Results of Celiac Ganglionectomy in the Treatment of Essential Hypertension, Annals of Surgery, Jun. 1938; 107(6): 909-916.
Cruickshank, J.M., Beta-Blockers Continue to Surprise Us, European Heart Journal (2000) 21, 354-364.
Curtis, John J. et al, Surgical Therapy for Persistent Hypertension After Renal Transplantation, Transplantation, vol. 31, No. 2, 1981, 125-128.
Dailey, U.G., Surgical Treatment of Hypertension: A Review-Part II, Journal of the National Medical Association, May 1948, vol. 40, No. 3., 113-116.
Dailey, U.G., Surgical Treatment of Hypertension: A Review-Part III, Journal of the National Medical Association, Jul. 1948, vol. 40, No. 4, 160-162.
Dailey, U.G., The Surgical Treatment of Hypertension: A Review, Journal of the National Medical Association, Mar. 1948, vol. 40, No. 2, 76-79.

(56) References Cited

OTHER PUBLICATIONS

Davis, Mark I. et al, Effectiveness of Renal Denervation Therapy for Resistant Hypertension A Systematic Review and Meta-Analysis, Journal of the American College of Cardiology, vol. 62, No. 3, 2013, 231-241.
De Wardener, H.E., The Hypothalamus and Hypertension, Physiological Reviews, vol. 81, No. 4, Oct. 2001.
Dequattro V. et al, The Sympathetic Nervous System: The Muse of Primary Hypertension, Journal of Human Hypertension, 2002, 16 (Supp 1), S64-S69.
Dibona, Gerald F. et al, Neural Control of Renal Function, Physiological Reviews, vol. 77, No. 1, Jan. 1997, 75-197.
Dibona, Gerald F. et al, Translational Medicine: The Antihypertensive Effect of Renal Denervation, Americal Journal of Physiology, 2010, 298, R245-R253.
Dibona, Gerald F., Neural Control of Renal Function: Cardiovascular Implications, Hypertension Journal of The American Heart Association, vol. 13, No. 6, Part 1, Jun. 1989, 539-548.
Dibona, Gerald F., Neural Control of the Kidney: Functionally Specific Renal Sympathetic Nerve Fibers, American Journal of Physiology, 2000, 279, R1517-R1524.
Dibona, Gerald F., Neural Control of the Kidney: Past, Present, and Future, Hypertension Journal of The American Heart Association, vol. 41, Mar. 2003, Part II, 621-624.
Dibona, Gerald F., Renal Innervation and Denervation: Lessons from Renal Transplantation Reconsidered, Artificial Organs, vol. 11, No. 6, 1987, 457-462.
Dibona, Gerald F., Role of the Renal Nerves in Renal Sodium Retention and Edema Formation, Trans Am Clin Climatol Assoc. 1990; 101: 38-45.
Dibona, Gerald F., Sympathetic Nervous System and Hypertension, Hypertension Journal of The American Heart Association, 2013; 61: 556-560.
Dibona, Gerald F., Sympathetic Nervous System and the Kidney in Hypertension, Curr Opin Nephrol Hypertens. Mar. 2002;11(2):197-200.
Dibona, Gerald F., The Sympathetic Nervous System and Hypertension, Hypertension Journal of The American Heart Association, Vo. 43, Feb. 2004, 147-150.
Doumas, Michael et al, Interventional Management of Resistant Hypertension, The Lancet, vol. 373, Apr. 11, 2009, pp. 1228-1230.
Dubuc, Marc et al, Feasibility of Cardiac Cryoablation Using a Transvenous Steerable Electrode Catheter, Journal of Interventional Cardiac Electrophysiology, 1998, 2: 285-292.
Elmula, Fadl et al, Renal Sympathetic Denervation in Patients With Treatment-Resistant Hypertension After Witnessed Intake of Medication Before Qualifying Ambulatory Blood Pressure, Hypertension. 2013;62:526-532.
Esler, M. et al, Sympathetic Nerve Activity and Neurotransmitter Release in Humans: Translation from Pathophysiology into Clinical Practice, Scandinavian Physiological Society, 2003, 177, 275-284.
Esler, Murray D. et al, Renal Sympathetic Denervation in Patients with Treatment-Resistant Hypertension (The Symplicity HTN-2 Trial): A Randomised Controlled Trial, Lancet, 2010; 376:1903-1909.
Esler, Murray et al, Assessment of Human Sympathetic Nervous System Activity from Measurements of Norepinephrine Turnover, Hypertension Journal of The American Heart Association, vol. 11, No. 1, Jan. 1988, 3-20.
Evelyn, Kenneth A. et al, Effect of Thoracolumbar Sympathectomy on the Clinical Course of Primary (Essential) Hypertension, American Journal of Medicine, Feb. 1960, 188-221.
Freyberg, R. H. et al, The Effect on the Kidney of Bilateral Splanchnicectomy in Patients with Hypertension, The Journal of Clinical Investigation, vol. 16, Issue 1, Jan. 1937, 49-65.
Gafoor, Sameer et al, Nonresponders to Renal Denervation for Resistant Hypertension, Endovascular Today, Oct. 2013, 63-70.
Garel, L. et al, Fatal Outcome After Ethanol Renal Ablation in Child with End-Stage Kidneys; AJR 146:593-594, Mar. 1986.
Gazdar, A. F. et al, Neural Degeneration and Regeneration in Human Renal Transplants, The New England Journal of Medicine, vol. 238, No. 5, Jul. 1970, 222-224.
Goldberg, Michael R. et al, Reconstructive Vascular Surgery for Renovascular Hypertension, Can Med Assoc J. Feb. 2, 1974;110(3):275-80.
Golwyn, Daniel H. et al, Percutaneous Transcatheter Renal Ablation with Absolute Ethanol for Uncontrolled Hypertension or Nephrotic Syndrome: Results in 11 Patients with End-Stage Renal Disease, Journal of Vascular and Interventional Radiology, Jul.-Aug. 1997, vol. 8, No. 4, 527-533.
Gorisch, Wolfram et al, Heat-Induced Contraction of Blood Vessels, Lasers in Surgery and Medicine 2:1-13 (1982).
Grassi, Guido et al, Baroreflex Control of Sympathetic Nerve Activity in Essential and Secondary Hypertension, Hypertension Journal of The American Heart Association, 1998;31:68-72.
Grassi, Guido et al, Dissociation Between Muscle and Skin Sympathetic Nerve Activity in Essential Hypertension, Obesity, and Congestive Heart Failure, Hypertension. 1998;31:64-67.
Grimson, Keith S. et al, Results of Treatment of Patients with Hypertension by Total Thoracic and Partial to Total Lumbar Sympathectomy, Splanchnicectomy and Celiac Ganglionectomy, Annals of Surgery, Jun. 1949, vol. 129, No. 6, 850-871.
Grimson, Keith S. et al, Total Thoracic and Partial to Total Lumbar Sympathectomy, Splanchnicectomy and Celiac Ganglionectomy for Hypertension, Annals of Surgery, Oct. 1953, vol. 138, No. 4, 532-547.
Grimson, Keith S., Total Thoracic and Partial to Total Lumbar Sympathectomy and Celiac Ganglionectomy in the Treatment of Hypertension, Annals of Surgery, Oct. 1941, vol. 114, No. 4, 753-775.
Guyton, Arthur C., Blood Pressure Control Special Role of the Kidneys and Body Fluids, Science, vol. 252, Jun. 1991, 1813-1816.
Hafkenschiel, Joseph H. et al, Primary Hypertension Survey of the Survival of Patients with Established Diastolic Hypertension After Ten Years of Medical and Surgical Treatment, The American Journal of Cardiology, vol. 16, Jul. 1965, 61-66.
Hafkenschiel, Joseph H. et al, The Surgical Treatment of Hypertension with Particular Reference to Andrenalectomy and Sympathectomy, Transactions. American College of Cardiology, vol. 5, Dec. 1955, pp. 107-112.
Hall, J.E. et al, Role of Sympathetic Nervous System and Neuropeptides in Obesity Hypertension, Brazilian Journal of Medical and Biological Research, 2000, 33:605-618.
Hall, John E., The Kidney, Hypertension, and Obesity, Hypertension. 2003;41:625-633.
Hall, Winthrop H. et al, Combined Embolization and Percutaneous Radiofrequency Ablation of a Solid Renal Tumor, American Journal of Roentgenology, 174, Jun. 2000, 1592-1594.
Hamm, Christian et al, Confluence, Issue eight, Apr. 2014.
Han, Young-Min et al, Renal Artery Embolization with Diluted Hot Contrast Medium: An Experimental Study, Journal of Vascular and Interventional Radiology, Jul. 2001;12(7):862-868.
Hansen, Jesper Melchoir et al, The Transplanted Human Kidney Does Not Achieve Functional Reinnervation, Clinical Science, (1994) 87, 13-20.
Heuer, George J., The Surgical Treatment of Essential Hypertension, Annals of Surgery, Oct. 1936, vol. 104, No. 3, 771-786.
Hinton, J. William, End Results of Thoracolumbar Sympathectomy for Advanced Essential Hypertension, The Bulletin, Apr. 1948, 239-252.
Holmer, Stephan et al, Role of Renal Nerves for the Expression of Renin in Adult Rat Kidney, The American Journal of Physiology, May 1994;266(5 Pt 2):F738-F745.
Hoobler, S.W. et al, The Effects of Splanchnicectomy on the Blood Pressure in Hypertension, Circulation Journal of The American Heart Association, vol. IV, Aug. 1951, 173-183.
Hoppe, Uta C. et al, Minimally Invasive System for Baroreflex Activation Therapy Chronically Lowers Blood Pressure with Pacemaker-like Safety Profile: Results from the Barostim Neo Ttrial, J Am Soc Hypertens. Jul.-Aug. 2012;6 (4):270-6.

(56) References Cited

OTHER PUBLICATIONS

Howard, James P. et al, Size of Blood Pressure Reduction from Renal Denervation: Insights from Meta-Analysis of Antihypertensive Drug Trials of 4121 Patients with Focus on Trial Design: the Converge Report, Heart 2013;0:1-9.

Howard, James P. et al, Unintentional Overestimation of an Expected Antihypertensive Effect in Drug and Device Trials: Mechanisms and Solutions, International Journal of Cardiology, vol. 172, Issue 1, Mar. 1, 2014, pp. 29-35.

Howell, Marcus H. et al, Tandem Stenting of Crossed Renal Arteries with Ostial Stenosis, Tex Heart Inst J. 2000; 27(2): 166-169.

Hoye, Neil A. et al, Endovascular Renal Denervation: A Novel Sympatholytic with Relevance to Chronic Kidney Disease, Clinical Kidney Journal Advance Access, (2013) 0: 1-8.

Huang, Shoei K. Stephen et al, Radiofrequency Catheter Ablation of Cardiac Arrhythmias, Basic Concepts and Clinical Applications, Wiley-Blackwell, Jun. 2000, 1-12.

Huang, Wann-Chu, Renal Denervation Prevents and Reverses Hyperinsulinemia-Induced Hypertension in Rats, Hypertension Journal of The American Heart Association, 1998;32:249-254.

Humpreys, Michael H., Renal Nerves and CKD: Is Renal Denervation the Answer?, Journal of The American Socity of Nephrology, 2012, 23: 1-3.

International Search Report and Written Opinion for Application No. PCT/US2010/054637 mailed Jan. 3, 2011.

International Search Report and Written Opinion for Application No. PCT/US2010/054684 mailed Jan. 10, 2011.

Irigoyen, M.C.C. et al, Baroreflex Control of Sympathetic Activity in Experimental Hypertension, Brazilian Journal of Medical and Biological Research, (1998) 31: 1213-1220.

Izzo, Jr, Joseph L. et al, The Sympathetic Nervous System and Baroreflexes in Hypertension and Hypotension, Current Hypertension Reports 1999, 3:254-263.

Young, Robert R. et al, Reversible Block of Nerve Conduction by Ultrasound Ultrasonic Blocking of Nerve Fibers, Arch Neurol. 1961;4(1):83-89.

Zazgornik, Jan et al, Bilateral Nephrectomy: The Best, but Often Overlooked, Treatment for Refractory Hypertension in Hemodialysis Patients, AJH 1998; 11:1364-1370.

Ritz, Eberhard, New Approaches to Pathogenesis and Management of Hypertension, Clin J Am Soc Nephrol 4: 1886-1891, 2009.

Robbins, Ivan M. et al, Pulmonary Vein Stenosis After Catheter Ablation of Atrial Fibrillation, Circulation Journal of The American Heart Association, 1998;98:1769-1775.

Rocha-Singh, Krishna J., Catheter-Based Sympathetic Renal Denervation A Novel Strategy for the Treatment of Resistant Hypertension, Endovascular Today, Aug. 2009, 52-56.

Rocha-Singh, Krishna J., Renal Artery Denervation: A Brave New Frontier, Endovascular Today, Feb. 2012, 45-53.

Sanderson, John E. et al, Effect of B-Blockade on Baroreceptor and Autonomic Function in Heart Failure, Clinical Science (1999) 96, 137-146.

Santos, Mario et al, Renal Sympathetic Denervation in Resistant Hypertension, World J Cardiol Apr. 26, 2013; 5(4): 94-101.

Savard, Sebastien et al, Eligibility for Renal Denervation in Patients With Resistant Hypertension When Enthusiasm Meets Reality in Real-Life Patients, J Am Coll Cardiol. 2012;60(23):2422-2424.

Schauerte, Patrick et al, Catheter Ablation of Cardiac Autonomic Nerves for Prevention of Vagal Atrial Fibrillation, Circulation Journal of The American Heart Association, 2000, 102:2774-2780.

Schlaich, Markus P. et al, International Expert Consensus Statement: Percutaneous Transluminal Renal Denervation for the Treatment of Resistant Hypertension, Journal of the American College of Cardiology vol. 62, Issue 22, Dec. 3, 2013, pp. 2031-2045.

Schlaich, Markus P. et al, Renal Denervation as a Therapeutic Approach for Hypertension Novel Implications for an Old Concept, Hypertension Journal of The American Heart Association, 2009;54:1195-1201.

Schlaich, Markus P. et al, Renal Sympathetic-Nerve Ablation for Uncontrolled Hypertension, The New England Journal of Medicine, 2009; 361:932-934.

Schmieder, Roland E. et al, ESH Position Paper: Renal Denervation—An Iterventional Therapy of Resistant Hypertension, Journal of Hypertension, 2012, 30:837-841.

Schmieder, Roland E. et al, Updated EHS Position Paper on Interventional Therapy of Resistant Hypertension, EuroIntervention 2013; 9:R58-R66.

Sellers, Alfred M. et al, Adrenalectomy and Sympathectomy for Hypertension Ten Year Survival, Archives of Surgery, vol. 89, Nov. 1964, 880-886.

Sen, S.K., Some Observations on Decapsulation and Denervation of the Kidney, The British Journal of Urology, vol. 8, Issue 4, Dec. 1936, 319-328.

Shiraki, Iwao William, Correction of Renal Hypertension by Ligation of Stenotic Segmental Renal Artery, Urology, vol. IX, No. 3, Mar. 1977, 296-298.

Shonai, Takaharu et al, Renal Artery Aneurysm: Evaluation with Color Doppler Ultrasonography Before and After Percutaneous Transarterial Embolization, J Ultrasound Med 19:277-280, 2000.

Silver, Donald et al, Renovascular Hypertension From Renal Artery Compression by Congenital Bands, Annals of Surgery, Feb. 1976, 161-166.

Smith, Gardner W. et al, Surgical Results and the Diagnostic Evaluation of Renovascular Hypertension, Annals of Surgery, May 1968, 669-680.

Smith, Harold P. et al, Radiofrequency Neurolysis in a Clinical Model Neuropathological Correlation, J Neurosurg 55:246-253, 1981.

Smithwick, R.H., An Evaluation of the Surgical Treatment of Hypertension, The Bulletin, Nov. 1949; 25(11):698-716.

Smithwick, Reginald H. et al, Splanchnicectomy for Essential Hypertension, The Journal of the American Medical Association, vol. 152, No. 16, Aug. 1953, 1501-1504.

Solis-Herruzo, J.A. et al, Effects of Lumbar Sympathetic Block on Kidney Function in Cirrhotic Patients with Hepatorenal Syndrome, Journal of Hepatology, 1987; 5: 167-173.

Sowers, James R. et al, Diabetes, Hypertension, and Cardiovascular Disease: An Update, Hypertension Journal of The American Heart Association, 2001;37:1053-1059.

Stanley, James C., Surgical Treatment of Renovascular Hypertension, The American Journal of Surgery, vol. 174, Aug. 1997, 102-110.

Stella, Andrea et al, Effects of Reversible Renal Denervation on Haemodynamic and Excretory Functions of the Ipsilateral and Contralateral Kidney in the Cat, Journal of Hypertension 1986, 4: 181-188.

Stuart, Candace, Newest Frontier in Cardiac Care: Kidneys; Cardiovascular Business, Dec. 13, 2012.

Stuart, Mary, Masterminds of Ardian: An Interview With Inventors Mark Gelfand and Howard Levin, Windhover Information, Start-Up Jan. 1, 2011.

Sun, Yingxian et al, Risk of Coronary Stenosis with Venous Ablation for Epicardial Accessory Pathways, PACE, Apr. 2001, Part II, vol. 24, 605.

Swartz, John F. et al, Radiofrequency Endocardial Catheter Ablation of Accessory Atrioventricular Pathway Atrial Insertion Sites, Circulation Journal of The American Heart Association, 1993;87:487-499.

Teigen, Corey L. et al, Segmental Renal Artery Embolization for Treatment of Pediatric Renovascular Hypertension, Journal of Vascular and Interventional Radiology, 1992; 3:111-117.

Teixeira, Maria Do Carmo et al,1992; Role of the Peripheral Renin Profile in Predicting Blood Pressure Control After Bilateral Nephrectomy in Renal-Transplanted Patients, Nephrol Dial Transplant (1998) 13: 2092-2097.

Teo, W S et al, Radiofrequency Catheter Ablation of Accessory Pathways: The Initial Experience in Singapore, Singapore Medical Journal, 1994; vol. 35:36-40.

Thiebot, J. et al, Bilateral Nephrectomy by Embolization of the Renal Arteries: A Report on Five Cases (author's transl), Sem Hop. Apr. 8-15, 1980;56(13-14):670-5.

(56) References Cited

OTHER PUBLICATIONS

Thomas, George et al, Renal Denervation to Treat Resistant Hypertension: Guarded Optimism, Cleveland Clinic Journal of Medicine, vol. 79, No. 7, Jul. 2012, 501-510.
Thomas, Natalie A., Secondary Consideration in Nonobviousness Analysis: The Use of Objective Indicia Following KSR V. Teleflex, NYU Law Review, vol. 86, No. 6, Dec. 2011, 2070-2112.
Ting, Chih-Tai et al, Arterial Hemodynamics in Human Hypertension Effects of Angiotensin Converting Enzyme Inhibition, Hypertension Journal of The American Heart Association, 1993;22:839-846.
Uchida, Fumiya et al, Effect of Radiofrequency Catheter Ablation on Parasympathetic Denervation: A Comparison of Three Different Ablation Sites, PACE, vol. 21, Nov. 1998, Part II, 2517-2521.
Valente, John F. et al, Laparoscopic Renal Denervation for Intractable ADPKD-Related Pain, Nephrol Dial Transplant (2001) 16:160.
Villarreal, Daniel et al, Effects of Renal Denervation on Postprandial Sodium Excretion in Experimental Heart Failure, American Journal of Physiology, May 1994;266(5 Pt 2):R1599-R1604.
Vonend, Oliver et al, Secondary Rise in Blood Pressure After Renal Denervation, The Lancet, vol. 380, Issue 9843, p. 778, Aug. 25, 2012.
Vujaskovic, Z. et al, Effects of Intraoperative Hyperthermia on Canine Sciatic Nerve: Histopathologic and Morphometric Studies, Int. J. Hyperthermia, 1994, Vol. 10, No. 6, 845-855.
Webb, R.L. et al, Functional Identification of the Central Projections of Afferent Renal Nerves, Clin. and Exper.—Theory and Practice, Ag(Suppl.I), 47-57 (1987).
Weinstock, Marta et al, Renal Denervation Prevents Sodium Retention and Hypertension in Salt-Sensitive Rabbits with Genetic Baroreflex Impairment, Clinical Science (1996) 90, 287-293.
Wilcox, Josiah N., Scientific Basis Behind Renal Denervation for the Control of Hypertension, Medtronic, Inc., Dec. 2012, 38 pages.
Winternitz, Sherry R. et al, Role of the Renal Sympathetic Nerves in the Development and Maintenance of Hypertension in the Spontaneously Hypertensive Rat, Journal of Clinical Investigation, vol. 66 Nov. 1980, 971-978.
Wolf-Maier, Katharina et al, Hypertension Treatment and Control in Five European Countries, Canada, and the United States, Hypertension. 2004;43:10-17.
Worthley, Stephen G. et al, Renal Denervation: How Do You Measure Success?, presentation 28 pages; Jul. 30, 2013.
Wyss, J.M. et al, Sensory Denervation of the Kidney Attenuates Renovascular Hypertension in the Rat, Am J Physiol Heart Circ Physiol 250:H82-H86, 1986.
Yamada, Yutaka et al, Age-Related Changes in Muscle Sympathetic Nerve Activity in Essential Hypertension, Hypertension Journal of The American Heart Association, 1989;13:870-877.
Jackman, Warren M. et al, Catheter Ablation of Arrhythmias, Proposed Anatomy and Catheter Ablation of Epicardial Posteroseptal and Left Posterior Accessory AV Pathways (Chapter 16), 2002, Futura Publishing Company, Inc., 321-343.
Jaff, Michael R. et al, Kidney Stenting Lowers Blood Pressure in Patients with Severe Hypertension; Catheterization and Cardiovascular Interventions; Published Online: Jun. 27, 2012 (DOI: 10.1002/ccd24449); Print Issue Date: Sep. 2012. URL: http://onlinelibrary.wiley.com/doi/10.1002/ccd.24449/abstract.
Jain, Mudit K. et al, A Three-Dimensional Finite Element Model of Radiofrequency Ablation with Blood Flow and Its Experimental Validation, Annals of Biomedical Engineering, vol. 28, pp. 1075-1084, 2000.
Jais, Pierre et al, Efficacy and Safety of Septal and Left-Atrial Linear Ablation for Atrial Fibrillation, The American Journal of Cardiology, vol. 84 (9A), Nov. 1999, 139R-146R.
Janssen, Ben J.A. et al, Frequency-Dependent Modulation of Renal Blood Flow by Renal Nerve Activity in Conscious Rabbits, American Journal of Physiology, 1997, 273:R597-R608.
Janssen, Ben J.A. et al, Renal Nerves in Hypertension, Miner Electrolyte Metab 1989;15:74-82.
Jin, Yu et al, No Support for Renal Denervation in a Meta-Analysis, JACC vol. 62, No. 21, 2013 Correspondence Nov. 19/26, 2013:2029-30.
Kaltenbach, Benjamin et al, Renal Artery Stenosis After Renal Sympathetic Denervation, J Am Coll Cardiol. Dec. 25, 2012;60(25):2694-5.
Kaltenbach, Benjamin et al, Renal Sympathetic Denervation as Second-Line Therapy in Mild Resistant Hypertension: A Pilot Study, Catheterization and Cardiovascular Interventions 81:335-339 (2013).
Kamiya, Atsunori et al, Parallel Resetting of Arterial Baroreflex Control of Renal and Cardiac Sympathetic Nerve Activities During Upright Tilt in Rabbits, Am J Physiol Heart Circ Physiol 298: H1966-H1975, 2010.
Kandzari, David E. et al, Catheter-Based Renal Denervation for Resistant Hypertension: Rationale and Design of the Symplicity HTN-3 Trial, Clin. Cardiol. 35, 9, 528-535 (2012).
Kapural, Leonardo et al, Radiofrequency Ablation for Chronic Pain Control, Current Pain and Headache Reports 2001, 5:517-525.
Kassab, Salah et al, Renal Denervation Attenuates the Sodium Retention and Hypertension Associated with Obesity, Hypertension vol. 25, No. 4, Part 2 Apr. 1995.
Katholi, Richard E. et al, Decrease in Peripheral Sympathetic Nervous System Activity following Renal Denervation or Unclipping in the One-Kidney One-Clip Goldblatt Hypertensive Rat, The Journal of Clinical Investigation, Jan. 1982;69(1):55-62.
Katholi, Richard E. et al, Role of the Renal Nerves in the Pathogenesis of One-Kidney Renal Hypertension in the Rat, Hypertension. 1981;3:404-409.
Katholi, Richard E. et al, The Role of Renal Sympathetic Nerves in Hypertension: Has Percutaneous Renal Denervation Refocused Attention on Their Clinical Significance?; Progress in Cardiovascular Disease 52 (2009) 243-248.
Katritsis, Demosthenes et al, Recurrence of Left Atrium-Pulmonary Vein Conduction Following Successful Disconnection in Asymptomatic Patients, Europace (2004) 6, 425e432.
Killip III, Thomas, Oscillation of Blood Flow and Vascular Resistance During Mayer Waves, Circulation Research, vol. XI, Dec. 1962, 987-993.
Kingwell, Bronwyn A. et al, Assessment of Gain of Tachycardia and Bradycardia Responses of Cardiac Baroreflex, Am J Physiol Heart Circ Physiol 260:H1254-H1263, 1991.
Kirchheim, H. et al, Sympathetic Modulation of Renal Hemodynamics, Renin Release and Sodium Excretion, Klin Wochenschr (1989) 67: 858-864.
Klein, GE et al, Endovascular Treatment of Renal Artery Aneurysms with Conventional Non-Detachable Microcoils and Guglielmi Detachable Coils, Br J Urol. Jun. 1997; 79(6):852-860.
Knight, Eric L. et al, Predictors of Decreased Renal Function in Patients with Heart Failure During Angiotensin-Converting Enzyme Inhibitor Therapy: Results from the Studies of Left Ventricular Dysfunction (SOLVD), American Heart Journal, vol. 138, No. 5, Part 1, Nov. 1999, 849-855.
Koepke, John P. et al, Functions of the Renal Nerves, The Physiologist, vol. 28, No. 1, Feb. 1985, 47-52.
Kompanowska-Jezierska, Elzbieta et al, Early Effects of Renal Denervation in the Anaesthetised Rat: Natriuresis and Increased Cortical Blood Flow, Journal of Physiology (2001), 531.2, pp. 527-534.
Krum, Henry et al, Catheter-Based Renal Sympathetic Denervation for Resistant Hypertension: A Multicentre Safety and Proof-of-Principle Cohort Study, www.thelancet.com vol. 373 Apr. 11, 2009 1275-1281.
Krum, Henry et al, Device-Based Antihypertensive Therapy: Therapeutic Modulation of the Autonomic Nervous System, Circulation. 2011;123:209-215.
La Grange, Ronald G. et al, Selective Stimulation of Renal Nerves in the Anesthetized Dog: Effect on Renin Release During Controlled Changes in Renal Hemodynamics, Circulation Research, Journal of The American Heart Association, 1973;33:704-712.
Labeit, Alexander Michael et al, Changes in the Prevalence, Treatment and Control of Hypertension in Germany? A Clinical-Epidemiological Study of 50.000 Primary Care Patients, PLOS One, Dec. 2012, vol. 7, Issue 12, e52229, 1-11.
Labonte, Sylvain, Numerical Model for Radio-Frequency Ablation of the Endocardium and its Experimental Validation, IEEE Transactions on Biomedical Engineering, vol. 41, No. 2. Feb. 1994, 108-115.

(56) References Cited

OTHER PUBLICATIONS

Lambert, Gavin W. et al, Health-Related Quality of Life After Renal Denervation in Patients With Treatment-Resistant Hypertension, Hypertension. 2012;60:1479-1484.

Lee, Sang Joon et al, Ultrasonic Energy in Endoscopic Surgery, Yonsei Medical Journal, vol. 40, No. 6, pp. 545-549, 1999.

Leertouwer, Trude C. et al, In-Vitro Validation, with Histology, of Intravascular Ultrasound in Renal Arteries, Journal of Hypertension 1999, vol. 17 No. 2, 271-277.

Leishman, A.W.D., Hypertension—Treated and Untreated, British Medical Journal, May 1959, 1361-1368.

Leonard, Bridget L. et al, Differential Regulation of the Oscillations in Sympathetic Nerve Activity and Renal Blood Flow Following Volume Expansion, Autonomic Neuroscience: Basic and Clinical 83 (2000) 19-28.

Levin, Stephen, Ardian: Succeeding Where Drugs Fail Treating Hypertension in the Cath Lab, In Vivo: The Business & Medicine Report, vol. 27, No. 10, Nov. 2009.

Litynski, Grzegorz S., Kurt Semm and the Fight against Skepticism: Endoscopic Hemostasis, Laparoscopic Appendectomy, and Semm's Impact on the "Laparoscopic Revolution", JSLS. Jul.-Sep. 1998; 2(3): 309-313.

Lu, David S.K. et al, Effect of Vessel Size on Creation of Hepatic Radiofrequency Lesions in Pigs: Assessment of the "Heat Sink" Effect, American Journal of Radiology, 178, Jan. 2002, 47-51.

Luscher, Thomas F. et al, Renal Nerve Ablation After Symplicity HTN-3: Confused at the Higher Level?; European Heart Journal, doi:10.1093/eurheartj/ehu195; May 14, 2014.

Lustgarten, Daniel L. et al, Cryothermal Ablation: Mechanism of Tissue Injury and Current Experience in the Treatment of Tachyarrhythmias, Progress in Cardiovascular Diseases, vol. 41, No. 6 (May/June), 1999: pp. 481-498.

Mahfoud, Felix et al, Expert Consensus Document from the European Society of Cardiology on Catheter-Based Renal Denervation, European Heart Journal, Jul. 2013;34(28):2149-57.

Mancia, Giuseppe et al, Sympathetic Activation in the Pathogenesis of Hypertension and Progression of Organ Damage, Hypertension Journal of The American Heart Association, 1999, 34:724-728.

McGahan, John P. et al, History of Ablation, Tumor Ablation, 2005, pp. 3-16.

Medtronic, Inc., J.P. Morgan Healthcare Conference, Corrected Transcript, Jan. 13, 2014, Factset:Callstreet, www.callstreet.com.

Medtronic, Inc., Medtronic Announces U.S. Renal Denervation Pivotal Trial Fails to Meet Primary Efficacy Endpoint While Meeting Primary Safety Endpoint, www.medtronic.com, Jan. 9, 2014.

Medtronic, Inc., RDN Therapy with the Symplicity Renal Denervation System, Procedure Fact Sheet, www.medtronic.com, 2011.

Medtronic, Inc., Renal Denervation (RDN) Novel Catheter-based Treatment for Hypertension, Symplicity RDN System Common Q&A, 2011.

Medtronic, Inc., Scientific Basis Behind Renal Denervation for the Control of Hypertension, Dec. 2012, http://www.icimeeting.com/2012/images/stories/PDF/1448_Wilcox_I_Mon.pdf.

Mehdirad, Ali et al, Temperature Controlled RF Ablation in Canine Ventricle and Coronary Sinus using 7 Fr or 5 Fr Ablation Electrodes, PACE, vol. 21, Jan. 1998, Part II, 316-321.

Meredith, I T et al, Exercise Training Lowers Resting Renal But Not Cardiac Sympathetic Activity in Humans; Hypertension Journal of The American Heart Association, 1991;18:575-582.

Michaelis, Lawrence L. et al, Effects of Renal Denervation and Renin Depletion on the Renal Responses to Intravascular Volume Expansion, Ann Surg. Mar. 1972; 175(3): 424-430.

\* cited by examiner

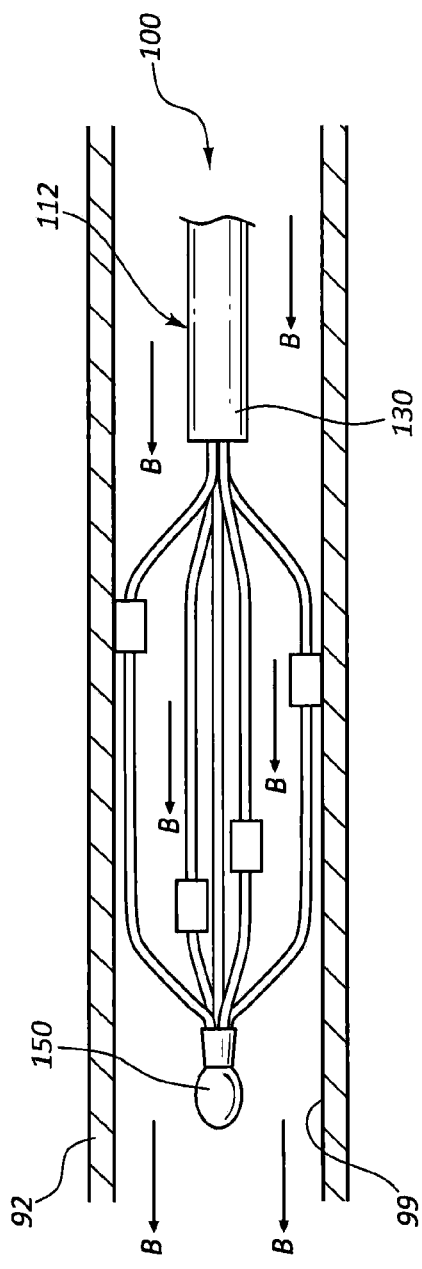
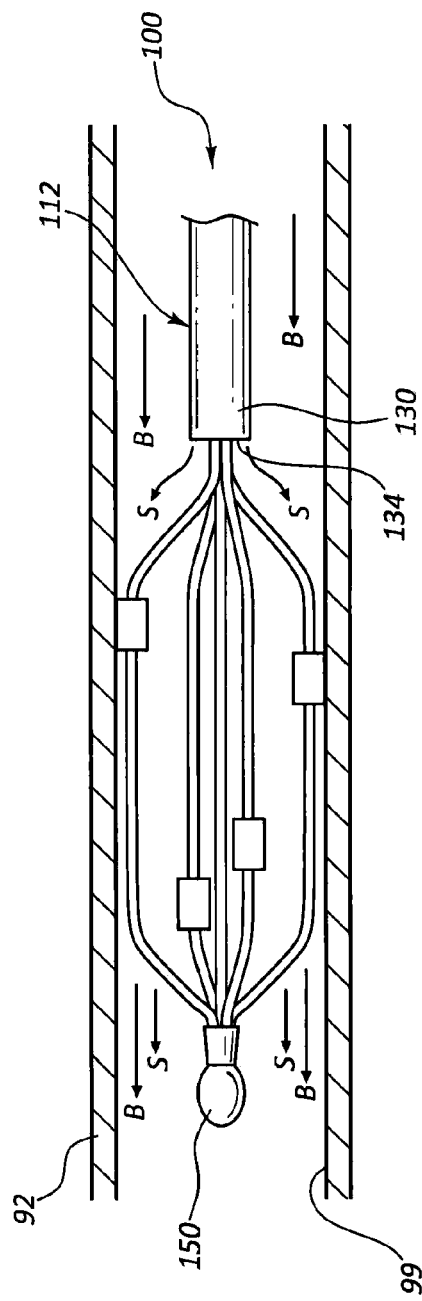
FIG. 6
FIG. 7

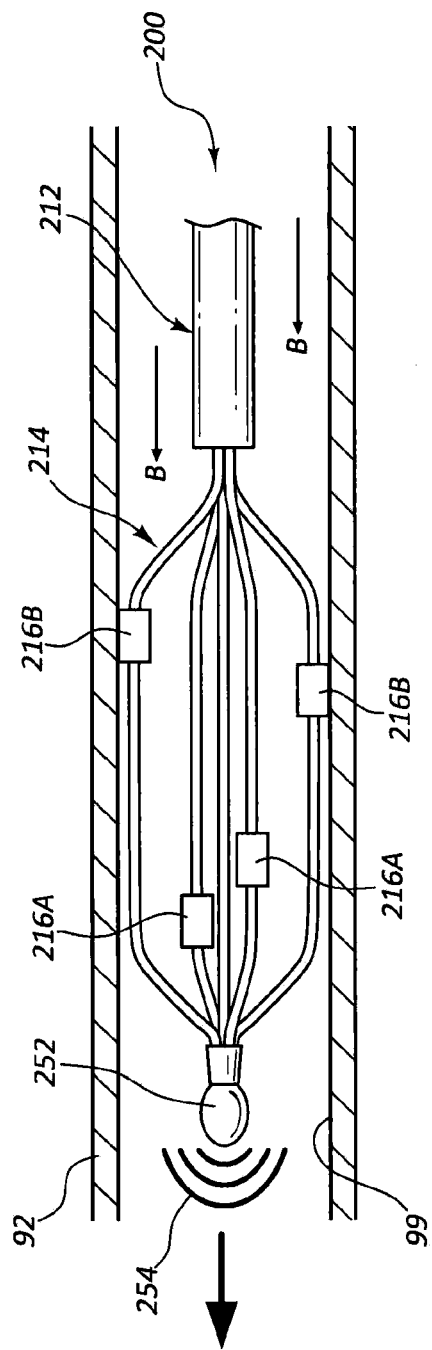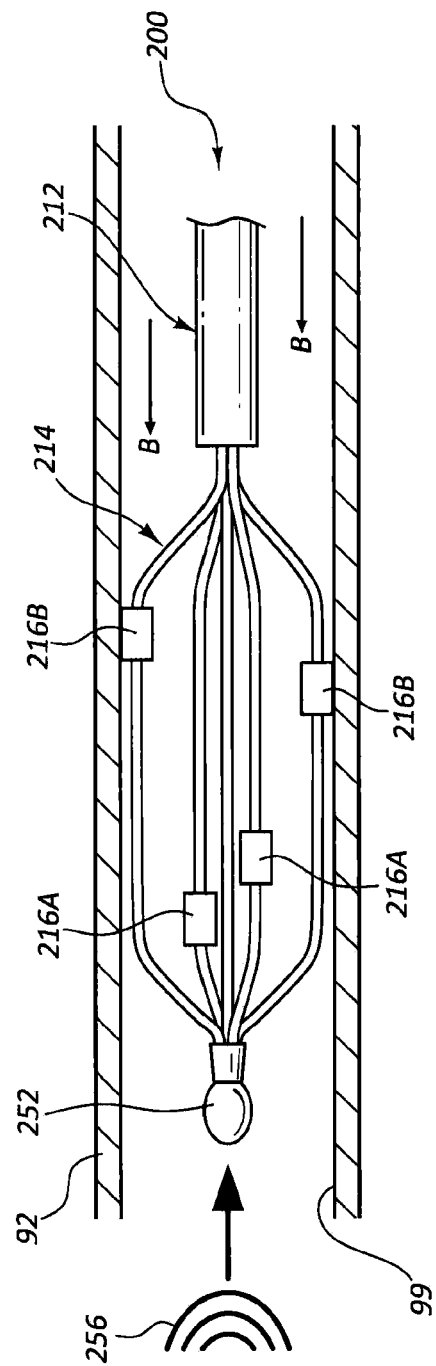

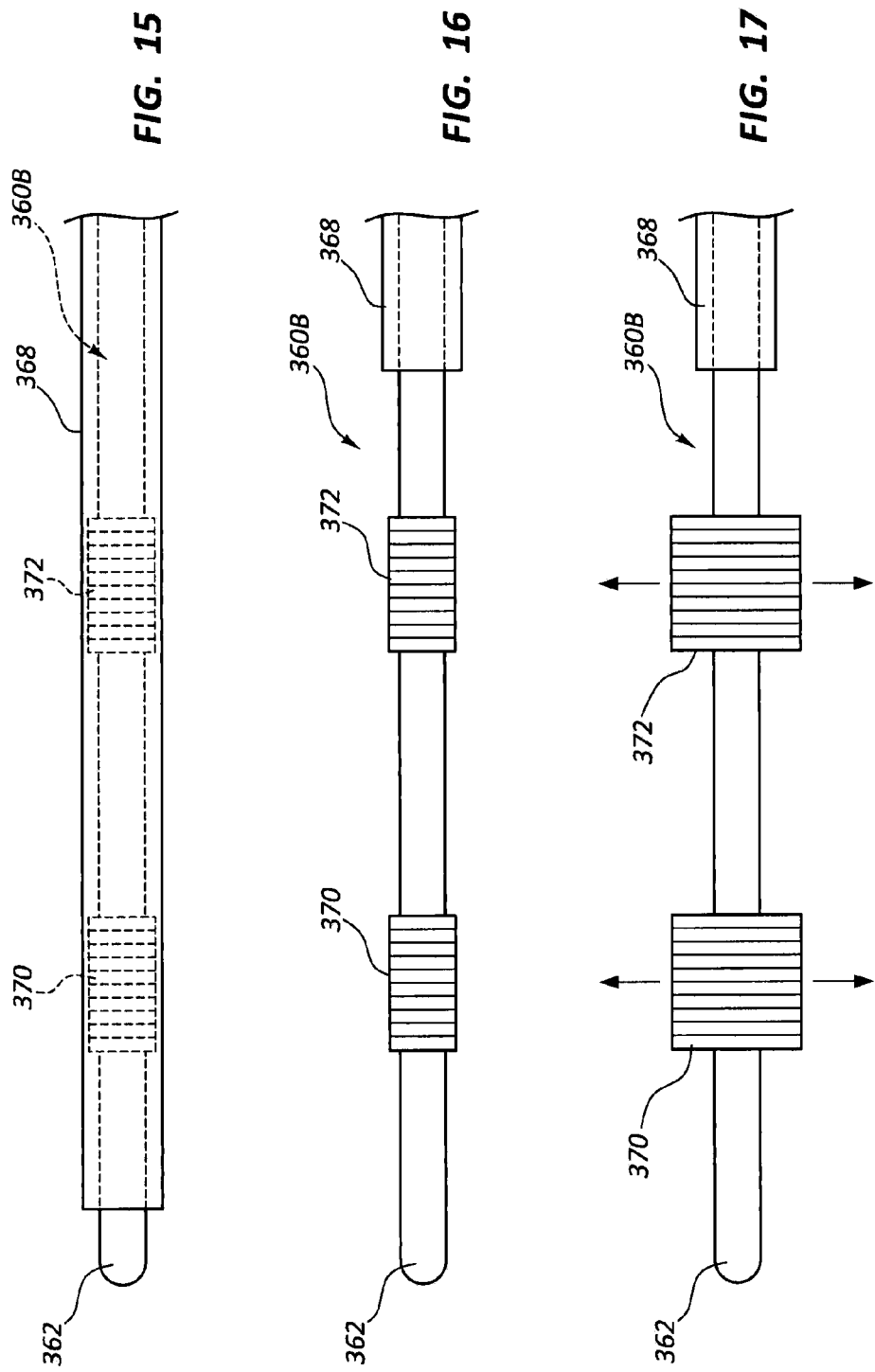

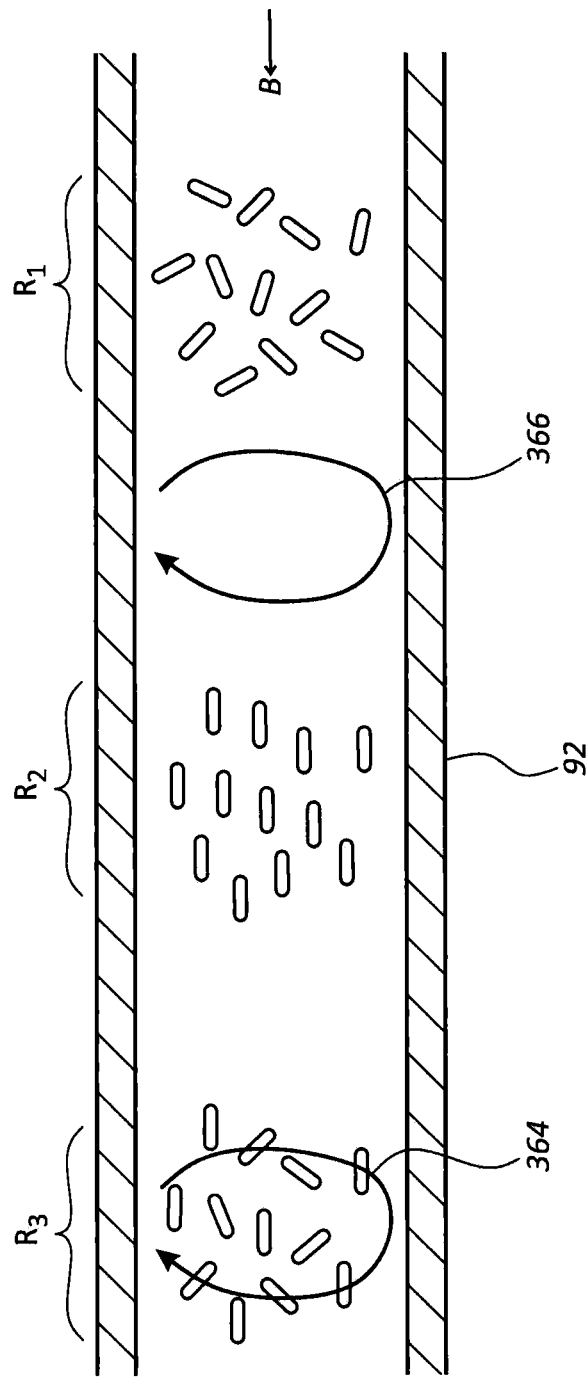

FEEDBACK SYSTEMS AND METHODS UTILIZING TWO OR MORE SITES ALONG DENERVATION CATHETER

TECHNICAL FIELD

The present disclosure relates generally to renal denervation system and methods, and more particularly, to systems and methods for assessing efficacy of a renal denervation procedure.

BACKGROUND

Renal denervation is a method whereby amplified sympathetic activities are suppressed. Amplified sympathetic activities and their associated systems are known to contribute to arterial hypertension. Thus, renal denervation is used to treat hypertension or other cardiovascular disorders and chronic renal diseases.

Renal denervation is achieved through destruction of afferent and efferent nerve fibers that run adjacent to the renal artery, which results in lower blood pressure in a patient. Renal denervation has also been shown to have benefits associated with treatment of heart failure, diabetes, obesity, sleep apnea, and ventricular tachycardia (VT). An established renal denervation procedure involves introducing a radiofrequency (RF) ablation catheter, which ablates renal nerves at 4 to 6 locations. The RF ablation catheter typically uses variable energy up to about 8 Watts. Usually, the operator's objective is to ablate at the lowest power possible for the least amount of time and at the fewest locations. Presently, no feedback mechanisms are available to provide the operator with insight about the efficacy of the renal denervation treatment during the treatment procedure. Thus, it is difficult for the operator to know whether further power and/or ablation locations are needed to accomplish adequate renal denervation.

SUMMARY

One aspect of the present disclosure relates to a renal denervation system having a renal denervation catheter and a flow determining system. The renal denervation catheter includes a plurality of ablation members positioned at a distal end portion thereof. The renal denervation catheter is insertable into a renal artery. The flow determining system includes a processor and first and second flow determining members spaced apart on the renal denervation catheter. The processor is configured to determine a change in blood flow through the renal artery resulting from a renal denervation procedure using the renal denervation catheter and in response to input from the first and second flow determining members.

The first flow determining member may include at least one fluid port configured to release a flow of fluid into the renal artery, the second flow determining member may include at least one sensor configured to detect the flow of fluid, and the processor may determine a time delay between releasing the flow of fluid and detecting the flow of fluid prior to and after treating the renal artery with the renal denervation catheter. A difference in the time delay prior to and after treating the renal artery with the renal denervation catheter may correspond to a change in blood flow.

The first flow determining member may include at least one first electrode and the second flow determining member may include at least one second electrode, and the processor may determine a change in impedance between the at least one first electrode and at least one second electrode, wherein the change in impedance corresponds to the blood flow. The at least one first electrode may include distal and proximal electrodes configured to deliver current, and the at least one second electrode may include at least two middle electrodes spaced between the distal and proximal electrodes and configured to measure voltage.

The renal denervation catheter may include a basket construction having a plurality of arms, and the plurality of ablation members may be positioned on separate ones of the plurality of arms. The first and second flow determining members may each include at least one pressure sensor, and the first and second flow determining members may be spaced apart along a length of the renal denervation catheter and configured to measure flow pressure within the renal artery. The first and second flow determining members may measure a pressure wave advanced through the renal artery in a first direction and reflected through the renal artery in an opposite second direction. The processor may determine a change in amplitude of the pressure wave reflected through the renal artery.

The first and second flow determining members may each include at least one wire coil, the first flow determining member may be configured to generate an electromagnetic field to orient dipoles of red blood cells in the blood flow passing through the at least one wire coil of the first flow determining member, and the red blood cells may induce current in the at least one wire coil of the second flow determining member. The renal denervation catheter may operate using one of radiofrequency and ultrasound.

Another aspect of the present disclosure relates to a method of determining the efficacy of a denervation procedure in a renal artery. The method includes providing a renal denervation catheter and a flow determining system, determining a preliminary flow characteristic of blood flow through the renal artery, ablating the renal artery with the renal denervation catheter as part of a renal denervation procedure, determining a subsequent flow characteristic of blood flow through the renal artery after ablating, and comparing the preliminary flow characteristic with the subsequent flow characteristic to determine a change in blood flow, which corresponds to the efficacy of the renal denervation procedure.

Determining the preliminary and subsequent flow characteristics may include injecting a flow of fluid into the blood flow at a first location and determining the presence of the flow of fluid at an axially spaced apart second location. Determining the preliminary and subsequent flow characteristics may include determining a change in impedance between at least first and second electrodes of the flow determining system, wherein the change in impedance corresponds to the change in blood flow. Determining the preliminary and subsequent flow characteristics may include determining a change in voltage between at least first and second electrodes of the flow determining system, wherein the change in voltage corresponds to the change in blood flow. Determining the preliminary and subsequent flow characteristics may include sensing with the flow determining system a pressure wave in the blood flow in a first direction and in an opposite second direction. Sensing the pressure wave may include determining an amplitude of the pressure wave. The flow determining system may include first and second coils, wherein the first coil is configured to generate an electromagnetic field that orients dipoles of red blood cells in the blood flow passing through the first coil, and the red blood cells induce a current in the second coil upon passing through the second coil downstream of the first coil.

Another aspect of the present disclosure relates to a method of determining blood flow in a renal artery during a renal denervation procedure. The method includes performing denervation on the renal artery, determining a blood flow characteristic prior to and after performing renal denervation, comparing the blood flow characteristic determined prior to and after performing renal denervation to determine whether blood flow has increased above a threshold level.

Determining the blood flow characteristic may include injecting a flow of fluid into the renal artery at a first location and determining the presence of the flow of fluid at a second location downstream of the first location. Determining the blood flow characteristic may include determining a change in impedance between at least first and second electrodes positioned on a renal denervation catheter. Determining the blood flow characteristic may include sensing an amplitude of a pressure wave in the blood flow in a first direction and in an opposite second direction. Determining the blood flow characteristic may include orienting dipoles of red blood cells in the blood flow at a first location, and passing the red blood cells through a coil at a downstream location to induce a current. Determining the blood flow characteristic may occur while a renal denervation catheter, which is used to perform the renal denervation procedure, is positioned in the renal artery.

The foregoing and other features, utilities, and advantages of the invention will be apparent from the following detailed description of the invention with reference to the accompanying drawings.

BRIEF DESCRIPTION OF THE DRAWINGS

The accompanying drawings illustrate various embodiments of the present disclosure and are a part of the specification. The illustrated embodiments are merely examples of the present disclosure and do not limit the scope of the invention.

FIG. 6 shows the renal denervation catheter of FIG. 5 positioned in a renal artery.

FIG. 7 shows the renal denervation catheter of FIG. 5 positioned in a renal artery and a detectable fluid being injected into the renal artery.

FIG. 8 shows another example renal denervation catheter in accordance with the present disclosure and positioned within a renal artery with a forward pressure wave present.

FIG. 9 shows the renal denervation catheter of FIG. 8 positioned in a renal artery with a reflected pressure wave present.

FIG. 15 shows another example blood alignment member positioned in a carrier tube in accordance with the present disclosure.

FIG. 16 shows the blood alignment member of FIG. 15 removed from the carrier tube and having a pair of expandable coils in an unexpanded position.

FIG. 17 shows the blood alignment member of FIG. 16 with the pair of expandable coils in an expanded position.

FIG. 18 schematically shows a plurality of red blood cells flowing through a renal artery and coils of one of the blood alignment members of FIGS. 13-17.

Throughout the drawings, identical reference numbers designate similar, but not necessarily identical, elements.

DETAILED DESCRIPTION

Figure 1:
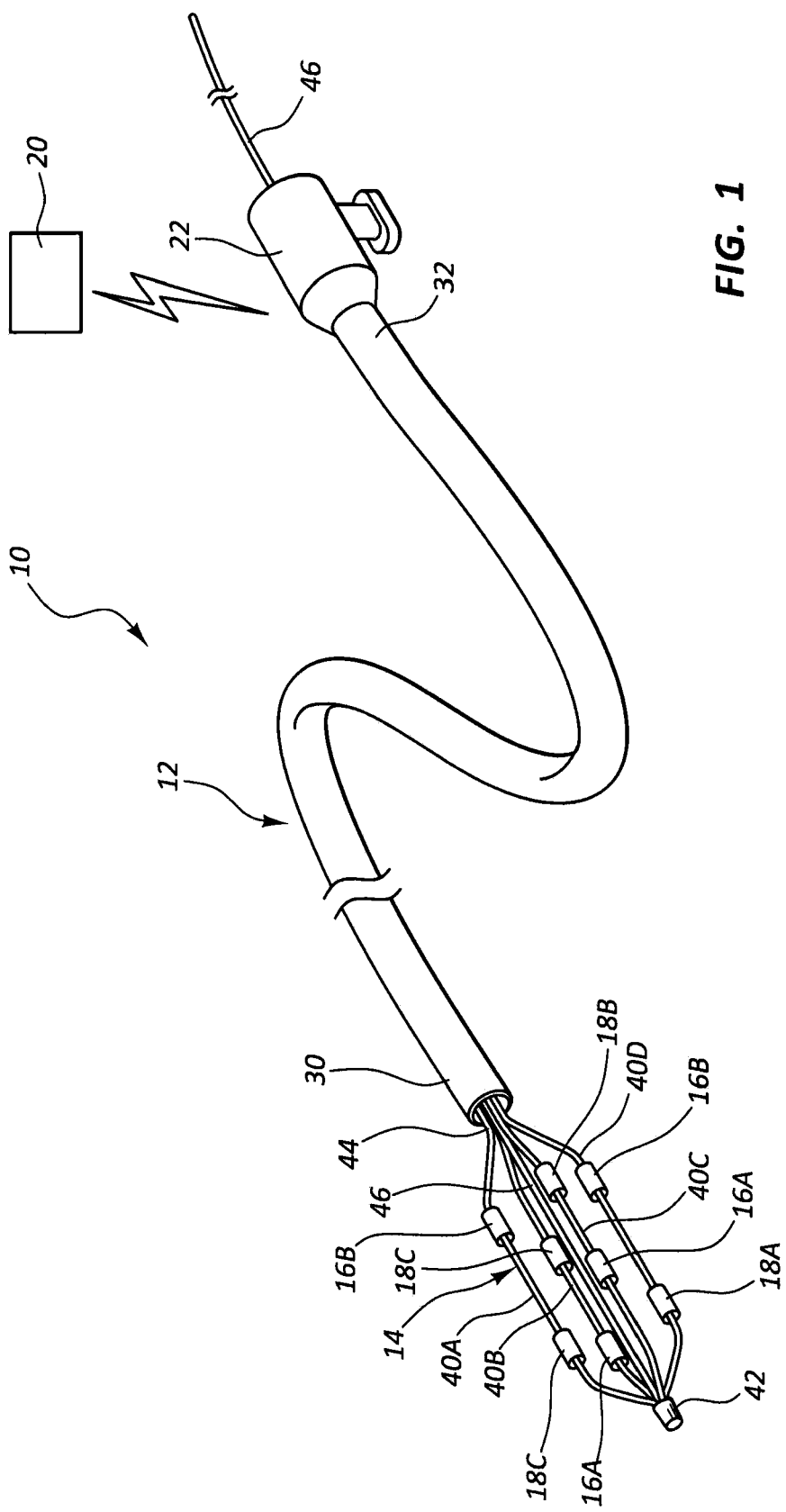
FIG. 1 is a perspective view of an example renal denervation catheter in accordance with the present disclosure.

The systems and methods disclosed herein are directed to aspects of renal denervation in a patient. The principles disclosed herein may be applicable to other systems and methods used for treating other aspects of the body, including, for example, any portion of the gastrointestinal, cardiovascular, nervous, hormonal, respiratory, excretory and reproductive systems of the body.

Renal denervation includes ablation of the renal artery using an ablation catheter. The systems and methods disclosed herein are used to provide feedback to an operator concerning the efficacy of the renal denervation procedure. The feedback may be given during the procedure, such as after ablating the renal artery while the ablation catheter is still positioned within the renal artery. It will be appreciated that the systems and methods disclosed herein may be applicable to other procedures involving ablation and other types of renal denervation procedures.

The general structure and function of renal denervation catheters used for ablating tissue in the renal artery are well known in the art. The principles disclosed herein may be useful in conjunction with various renal denervation catheters and methods of conducting renal denervation procedures. One procedure for renal denervation includes introducing a radio frequency ablation catheter into the renal artery and ablating renal nerves at several locations using variable energy up to, for example, about 8 Watts. The locations may be determined by a plurality of pre-positioned ablation members arranged in contact with an interior surface of the renal artery at various axially and circumferentially spaced apart locations. The ablation catheter may be repositioned axially and circumferentially at various locations in the renal artery to perform multiple ablations. In other examples, a single ablation member is moved to a plurality of axial and circumferential positions within the renal artery to ablate the renal nerves. Multiple series of stimulating, measuring and ablating may be used to confirm efficacy of the denervation procedure. Further, there may not be direct communication between any specific electrodes.

The renal denervation catheters of the present disclosure may provide feedback mechanisms for determining the efficacy of the procedure while the procedure is ongoing (i.e., feedback in real time), or at least while the renal denervation device is positioned within the patient. The devices and methods disclosed herein provide for measuring the effect of renal denervation using two or more sites along a length of the renal artery (e.g., along the length of a renal denervation catheter or renal denervation system component). The systems and methods may be used to determine flow characteristics in blood flow through the renal artery pre-ablation and post-ablation, and compare those flow characteristics to determine the efficacy of the renal denervation procedure.

In a first example, described with reference to FIGS. 1-4, a plurality of electrodes may be placed along the length of a renal denervation catheter, and impedance is measured between the electrodes before and after a denervation procedure during which the renal artery is ablated. Since vasodilation should occur due to the ablation, the impedance should decrease after the ablation occurs. In one example, four electrodes are spaced apart along a length of the renal denervation catheter. The distal-most and proximal-most electrodes may be used to deliver current, and the middle electrodes, which are positioned axially between the distal-most and proximal-most electrodes, may be used to measure voltage for the impedance measurement. As the renal artery dilates in response to a renal denervation procedure, more blood surrounds the electrodes and the electrodes have reduced contact with the inner surface of the renal artery, thereby causing a decrease in impedance.

FIG. 1 shows an example renal denervation catheter 10 having a catheter shaft 12, a deployable basket 14, ablation electrodes 16A,B, impedance electrodes 18A-C, a controller 20, and a hub 22. The deployable basket 14 may be operable between retracted and expanded positions. When in the expanded position, the deployable basket 14 positions the ablation electrodes 16A,B and impedance electrodes 18A-C in contact with an inner surface of a renal artery. The controller 20 may control the ablation electrodes 16A,B and impedance electrodes 18A-C to perform a renal denervation procedure by ablating renal nerves associated with the renal artery, and determine efficacy of the renal denervation procedure using a change in impedance. The controller 20 may be referred to as or include a processor or microprocessor. The ablation electrodes 16A,B may include radio frequency (RF) electrodes. In other embodiments, the ablation electrodes 16 may include other types of energy sources such as, for example, ultrasound electrodes, laser, cryothermal, and microwave energy sources.

The catheter shaft 12 may include distal and proximal ends 30, 32. A deployable basket 14 may include a plurality of splines 40A-D, distal and proximal ends 42, 44, and a pull wire 46. The deployable basket 14 may be operable between a retracted position and the expanded position shown in FIG. 1 by applying a tension force in the pull wire 46 while maintaining the proximal end 44 fixed relative to the catheter shaft 12. The ablation electrodes 16A,B and impedance electrodes 18A-C may be mounted to the splines 40A-D. In one example, one ablation electrode and one impedance electrode are mounted to each of the splines 40A-D. The ablation electrodes 16A,B may be positioned at spaced apart locations along a length of the deployable basket 14 and at circumferentially spaced apart locations. Likewise, the impedance electrodes 18A-C may be positioned at axially spaced apart locations along the length of the deployable basket 14 and at circumferentially spaced apart locations.

The ablation electrodes 16A,B may operate to deliver energy in the form of, for example, heat to a sidewall of the renal artery and renal nerves positioned within a sidewall and along an exterior surface of the renal artery. Varying an amount of energy delivered to the ablation electrode 16A,B and repositioning the deployable basket 14 at various locations axially and circumferentially within the renal artery may provide customized denervation of the renal artery and associated renal nerves.

The impedance electrodes 18A-C may be used to determine a change in impedance prior to and after denervation using the ablation electrodes 16A,B. In one example, one distal impedance electrode 18A and one proximal impedance electrode 18B are positioned at proximal and distal ends of the deployable basket 14, and a pair of middle impedance electrodes 18C may be positioned axially between the distal and proximal impedance electrodes 18A,B. IN other embodiments, multiple distal impedance electrodes 18A, multiple proximal impedance electrodes 18B, and any number of middle impedance electrodes 18C (e.g., only a single middle electrode 16C) may be used. The impedance electrodes 18A-C may be positioned on any one of the plurality of splines 40A-D, such as being positioned on separate ones of the splines 40A-D or consolidated on only some of the splines 40A-D. The distal and proximal impedance electrodes 18A,B may have a current delivered to them, and the middle impedance electrodes 18C may be used to measure voltage for an impedance measurement.

In other examples, the ablation electrodes 16A,B may also be used to deliver the current and measure voltage used for the impedance measurement. In some examples, four electrodes may be used to generate an impedance measurement. However, in other examples, any number of electrodes may be used, such as, for example, the four impedance electrodes 18A-C shown in FIGS. 1-4, eight electrodes (e.g., a combination of the ablation electrodes 16A,B and impedance electrodes 18A-C), or any other number of electrodes.

Figure 2:
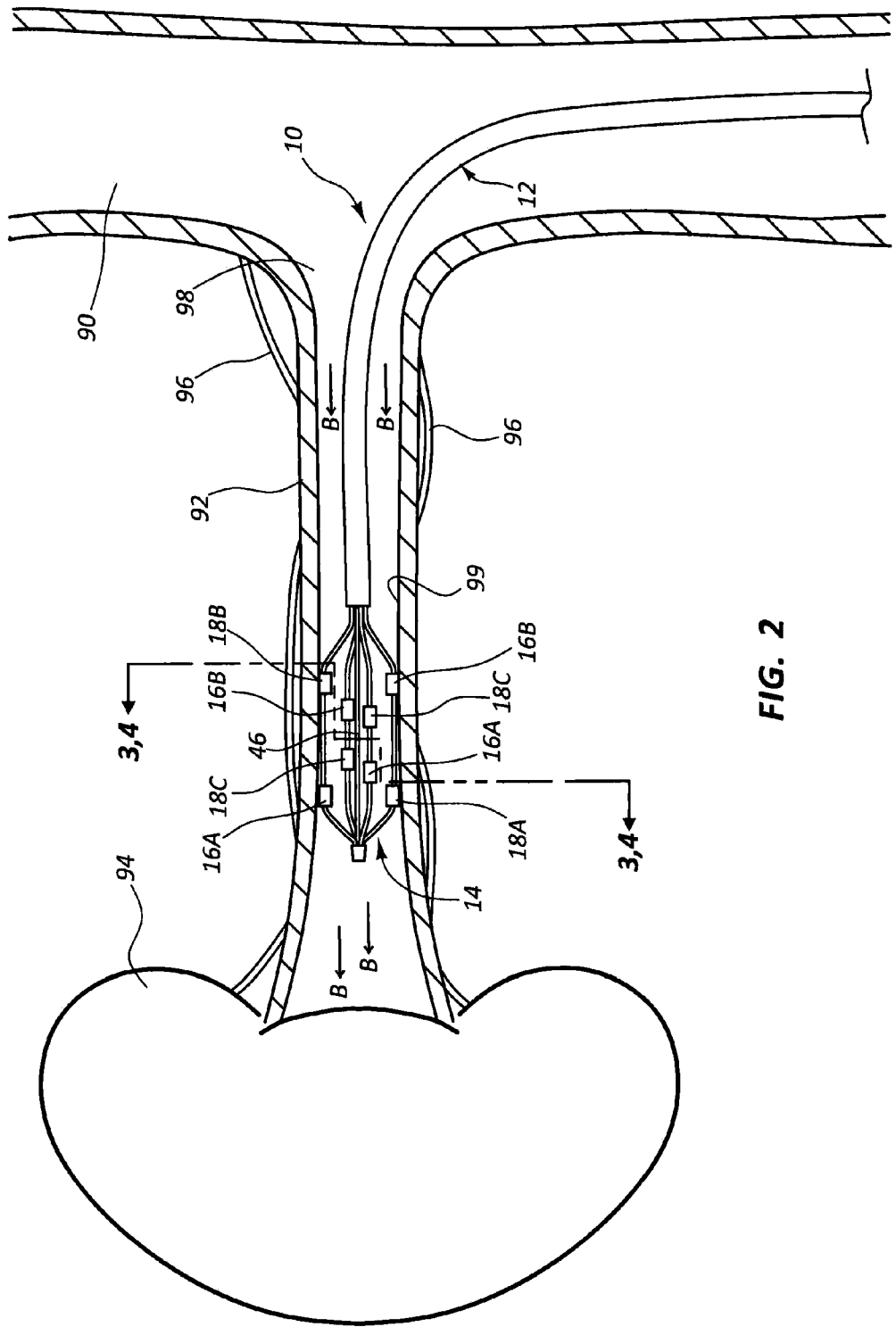
FIG. 2 shows the renal denervation catheter of FIG. 1 positioned in a renal artery.
Figure 4:
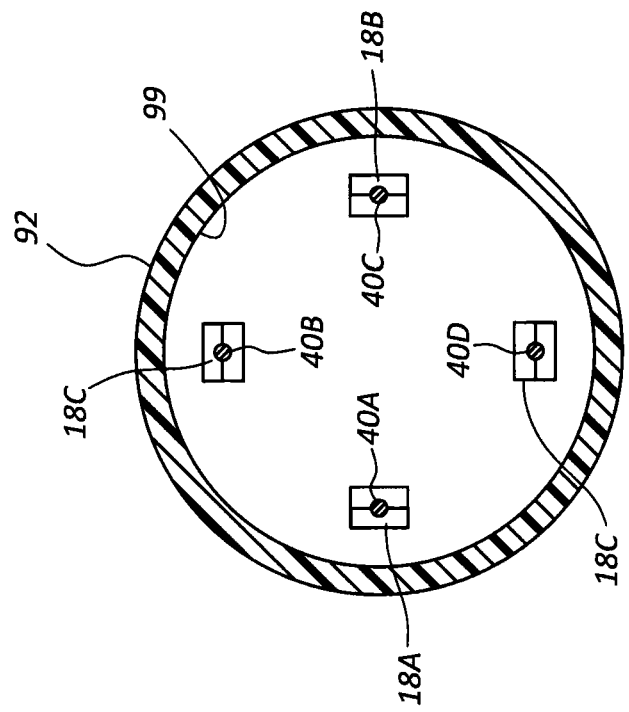
FIG. 4 is a cross-sectional of the renal denervation catheter and renal artery of FIG. 2 taken along cross-section indicators 4-4 after ablating the renal artery.

FIG. 2 shows the renal denervation catheter 10 advanced through the aorta 90 and into the renal artery 92. The deployable basket 14 may be positioned in the renal artery 92 upstream from the kidney 94 and downstream of an ostium 98 of the renal artery 92. A plurality of renal nerves 96 may extend along an exterior surface of the renal artery 92 and may be positioned at least partially within the sidewall of the renal artery 92. The deployable basket 14 may be expanded to contact the ablation electrodes 16A,B and impedance electrodes 18A-C against an inner surface 99 of the renal artery 92. Current may be delivered to some of the impedance electrodes 18A-C while other of the impedance electrodes 18A-C may be used to measure voltage for calculating an impedance measurement. The impedance measurement may be stored (e.g., using the controller 20) and compared to future calculated impedance measurements.

The operator may operate the ablation electrodes 16A,B to ablate the renal artery 92 and associated renal nerves 96. The ablation may be part of a renal denervation procedure. The ablation electrodes 16A,B may be controlled using the controller 20. Operating the ablation electrodes 16A,B may include, for example, controlling an amount of energy delivered to the electrodes, controlling a duration of application of energy, and determining a temperature of the electrode.

After the renal denervation using ablation electrodes 16A, B, current is again delivered to some of the impedance electrodes 18A-C while other of the impedance electrodes 18A-C measure voltage, which is used for determining a second impedance measurement. The second impedance measurement is compared to the first impedance measurement, which was determined prior to ablating. If the change in impedance falls within a certain range, or the absolute value of the second impedance measurement meets a threshold value, the renal denervation procedure may be considered successful. If the change in impedance or absolute value of the second impedance measurement does not meet predetermined values, the operator may choose to deliver additional energy to the ablation electrodes 16A,B for a second ablation. The second ablation may occur in the same position as the first ablation, or the operator may move the ablation electrodes 16A,B into different axial or circumferential positions within the renal artery 92 and then conduct further ablation with the ablation electrodes 16A,B. Further impedance measurements may be made using the impedance electrodes 18A-C after the second ablation to determine whether the renal denervation procedure has been successful. The success or efficacy of the renal denervation procedure may be determined during the denervation procedure generally, such as when the renal denervation catheter 10 is positioned within the renal artery 92.

Figure 3:
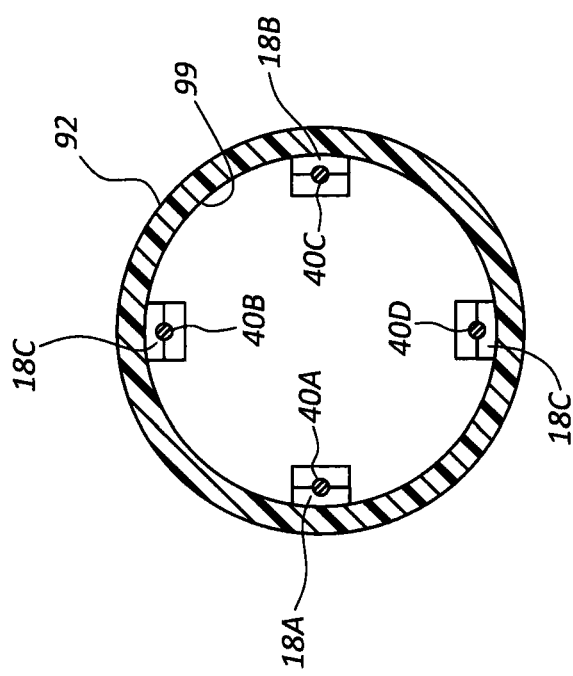
FIG. 3 is a cross-sectional view of the renal denervation catheter and renal artery of FIG. 2 taken along cross-section indicators 3-3 prior to ablating the renal artery.

FIG. 3 shows the impedance electrodes 18A-C prior to ablation. The impedance electrodes 18A-C may be in contact with the inner surface 99 of the renal artery 92. After ablation and successful renal denervation, there may be increased blood flow around the impedance electrodes 18A-C resulting from, for example, the impedance electrodes 18A-C moving out of contact with the inner surface 99 of the renal artery 92 or an increased volume of blood flow through the renal artery 92. The separation of the impedance electrodes 18A-C from the inner surface 99 after successful renal denervation may reduce impedance between the impedance electrodes 18A-C. The reduced impedance may also result from increased blood flow through the renal artery 92. Increased blood flow may result from reduced sympathetic tone and increased vasodilation in the renal artery and the glomerular capillaries and adjacent arterials associated with the kidney.

Other steps associated with the renal denervation procedure described with reference to FIG. 2 may include stimulating the renal nerves 96 prior to determining an impedance measurement and ablating the renal artery 92. The stimulation may be achieved by positioning the deployable basket 14 within the renal artery 92 adjacent to the ostium 98. The deployable basket 14 may be expanded to position the ablation electrodes 16A,B in contact with the inner surface 99 of the renal artery 92. Energy is supplied via the ablation electrode 16A,B to stimulate the renal nerves 96 without ablating. This electrode stimulation may generate a physiological response in the kidney 94 such as, for example, the increased production of rennin. After the operator determines that a successful renal denervation procedure has occurred using a change of impedance before and after ablating the renal artery 92 (e.g., as described above with reference to FIG. 2), the operator may again stimulate the renal nerves 96 by positioning the expanded deployable basket 14 at the ostium 98 and supplying an electrical stimulation to the renal nerves 96. If the renal denervation procedure was successful, there may be little or no physiological response from the kidneys resulting from the electrical stimulation.

The impedance-related devices and methods described with reference to FIGS. 1-4 may be extended into an approach of using two separate sites. In this example, a pulsatile impedance waveform may be used to decide the propagation of velocity pre-ablation and post-ablation. For example, the time delay of dZ/dtmax at the two sites (e.g., distal and proximal ends on the deployable basket 14 where Z is an impedance measurement) pre-ablation and post-ablation may be used to assess flow velocity pre-renal denervation and post-renal denervation. The flow velocity may be used to measure the ablation outcome together with other parameters.

Figure 5:
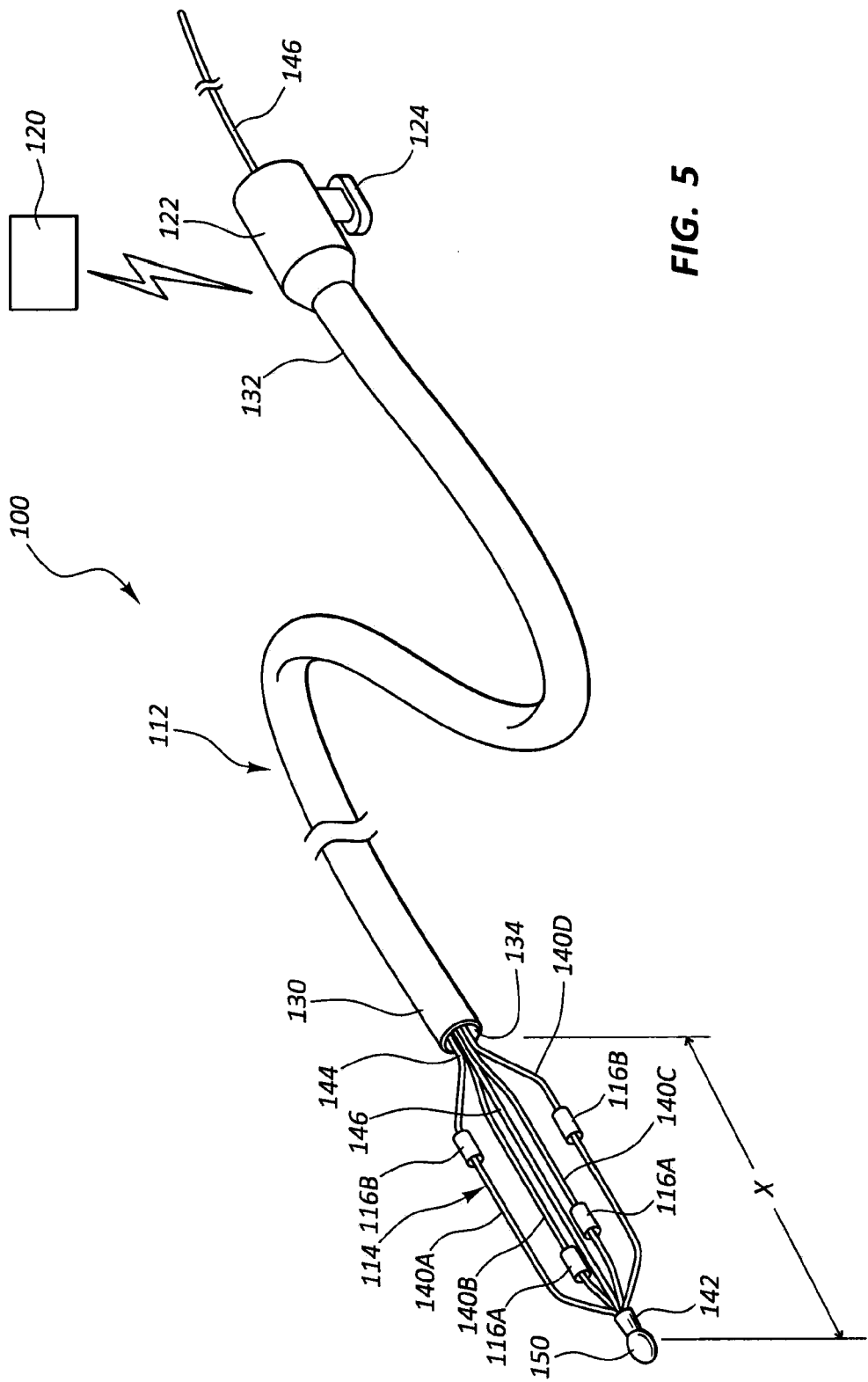
FIG. 5 is a perspective view of another example renal denervation catheter in accordance with the present disclosure.

Referring now to FIGS. 5-7, another example system and method for renal denervation is shown and described. The renal denervation catheter 100 shown in FIGS. 5-7 includes at least one port for injecting a substance into a blood flow B in the renal artery 92, and a sensor positioned downstream of the port to determine the presence of the substance in the blood flow B. The sensor may include, for example, one of an optical sensor, a chemical sensor, and a Doppler sensor. The substance may include, for example, a contrast agent or fluid having certain physical or chemical properties that are detectable within the blood flow. Prior to ablating the renal artery as part of a renal denervation procedure, the substance may be injected into the blood stream, with the downstream sensor detecting the presence of the substance within a measureable time period after the injection. After ablating the renal artery, the substance is again injected into the blood flow, with the sensor again detecting the presence of the substance within a measureable time period after the injection. The time period before and after ablation are compared. If the change in time or an absolute value of the amount of time after ablation meets a threshold value, the operator may determine whether the ablation and associated denervation is sufficient.

Referring to FIG. 5, a renal denervation catheter 100 includes a catheter shaft 112, a deployable basket 114, a plurality of ablation electrodes 116A,B, a controller 120 and a hub 122. The catheter shaft 112 includes distal and proximal ends 130, 132, and a lumen 134. The deployable basket 114 includes a plurality of splines 140A-D, distal and proximal ends 142, 144, and a pull wire 146. The renal denervation catheter 100 may include a sensor 150 positioned downstream of the distal opening of the lumen 134 (e.g., at the distal end 130). The sensor 150 may include any of a number of different types of sensors including, for example, an optical sensor, a chemical sensor, and a Doppler sensor. The sensor 150 may operate to determine presence of a substance that is injected into the blood flow from the lumen 134 of catheter shaft 112. The lumen 134 may be in flow communication with a port 124 on hub 122. The lumen 134 may include a distal port near the distal end 130 of catheter shaft 112. The substance may include, for example, a contrast agent or other fluid that is detectable by the sensor 150.

The sensor 150 may be positioned at any desirable location. In one example, the sensor 150 is positioned at the distal end 142 of the deployable basket 114. The sensor may be positioned at other locations such as, for example, on one or more of the splines 140A-D or the pull wire 146. The sensor may be positioned on the catheter shaft and an outlet port for the substance S to be injected into the renal artery is positioned upstream of the sensor. The sensor may communicate its measurements back to the controller (e.g., controller 20) or directly to the operator. The sensor may be connected using, for example, a hardwire connection or a wireless communication such as radio frequency (RF).

Referring to FIG. 6, the renal denervation catheter 100 is positioned in a renal artery 92 as part of a renal denervation procedure. The substance S is injected into the renal artery 92 and flows downstream with the blood flow B as shown in FIG. 7. The sensor 150 detects the presence of substance S. A time period $T_1$ for the substance S to travel from the port in lumen 134 to the sensor 150 is determined and stored for comparison to future determined time periods. Thereafter, the ablation electrodes 116A,B are operated to ablate the renal artery 92 and associated renal nerves. The substance S is again injected into the blood flow B and detected downstream with the sensor 150. A second time period $T_2$ is determined for travel of the substance S from the point of injection until being sensed by the sensor 150. The times $T_1$ and $T_2$ are compared to determine a $\Delta T$. If $\Delta T$ meets a threshold value, the renal denervation may be considered successful. Alternatively, if $T_2$ meets a certain predetermined absolute value, the renal denervation procedure may be considered successful. Thereafter, the operator may remove the renal denervation catheter 100 from the renal artery 92. If $\Delta T$ or $T_2$ do not meet threshold values, the operator may choose to conduct further ablation of the renal artery 92 followed by additional measurements of $\Delta T$ and T.

The time period between injecting the substance S and detecting the substance S with sensor 150 may be based at least in part on a time at which the substance S is initially injected into lumen 134 at port 124 as opposed to when the substance S is injected out of the lumen 134 into the blood flow B. The distance between the sensor 150 and a distal port of the lumen 134 where the substance is injected may have a distance X as shown in FIG. 5. The distance X may vary depending on, for example, the sensitivity of the sensor 150 or the type of substance S being used. The distal port for lumen 134 may be positioned at the distal end 130, or may be positioned along a portion of the catheter shaft 112 that is positioned within the renal artery 92 during the renal denervation procedure.

It is expected that there will be an increase in blood flow after the renal denervation procedure, which results in an increase in mean or peak velocity of blood flow. Therefore, the time T for detecting the substance S should decrease by a certain amount after ablation. There may be a threshold by which $\Delta T$ or $T_2$ decreases in order for the ablation to be considered effective. In one example, the sensor is a near-infrared spectroscopy (NIRS) optical sensor, and the substance S includes incyanine green (ICG) or another contrast agent such as SIDAG (1,1(')-bis-(4-sulfobutyl) indotricarbocyanine-5,5(')-dicarboxylic acid diglucamide monosodium salt).

Prior to renal denervation, the substance is injected (e.g., as a contrast agent) through the distal port of lumen 134 at a time A. The substance is then detected by the sensor 150 at a time B. The time $T_1$ for the substance to travel from the port to the sensor 150 is the time B minus the time A. After renal denervation, the substance may be injected and a time $T_2$ determined using the sensor 150. The times $T_1$ and $T_2$ are compared to determine $\Delta T$ as described above.

Referring now to FIGS. 8-12, another example system and method for renal denervation is described. In this example, a pressure wire or other pressure sensor is used to measure the morphology of a traveling pressure wave in the renal artery. The pressure wave at any given point along an artery may include a forward wave caused by the force of ejection from the left ventricle (LV) into a close system of tubes, along with a delayed reflection wave that results from the forward wave meeting a resistance of glomerular capillaries and adjacent arterioles. The arterial pressure wave form at any location may be represented as a superimposed sum of forward and reflected pressure waves.

FIG. 8 shows a renal denervation catheter 200 positioned within a renal artery 92. The renal denervation catheter 200 includes a catheter shaft 212, a deployable basket 214, a plurality of ablation electrodes 216A,B and a pressure sensor 252. A forward pressure wave 254 advances through the renal artery 92 in the direction of blood flow B. FIG. 9 shows a reflected pressure wave 256 traveling in a direction opposite the blood flow B. The pressure sensor 252 may detect the forward pressure wave 254 and reflected pressure wave 256. A pressure wave form 250 may be determined as a sum of the absolute value of the forward and reflected pressure wave 254, 256.

Figure 10:
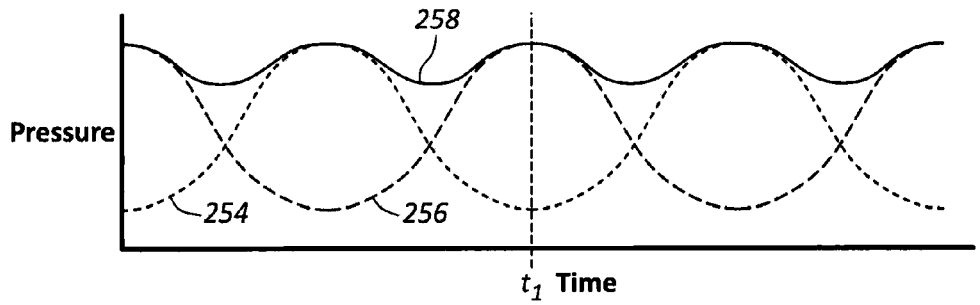
FIG. 10 is a graph showing a pressure waveform measured at a proximal arterial location, decomposed into forward and reflected pressure waves.

FIG. 10 is a graph showing the forward and reflected pressure waves 254, 256 that are present at a proximal location in the aorta. The pressure wave form 258 in the aorta has a generally high value over time.

Figure 11:
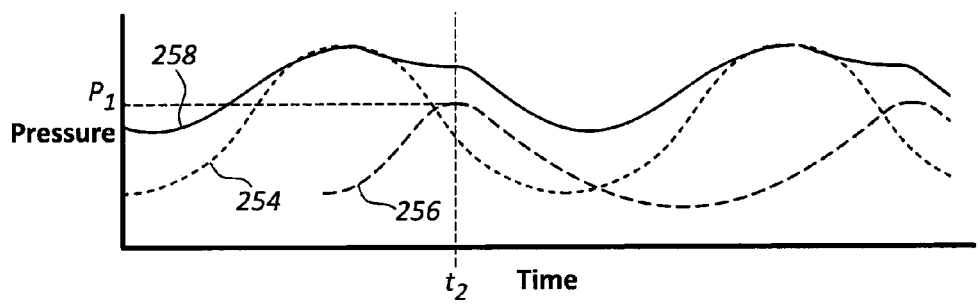
FIG. 11 is a graph showing a pressure waveform measured in a renal artery prior to ablation, decomposed into forward and reflected pressure waves.

FIG. 11 is a graph showing the forward and reflected pressure waves 254, 256 and pressure wave form 258 in the renal artery 92 prior to renal denervation. The reflected pressure wave 256 has a relatively high value due to the resistance of blood flow through the renal artery and downstream blood flow paths in the kidney.

Figure 12:
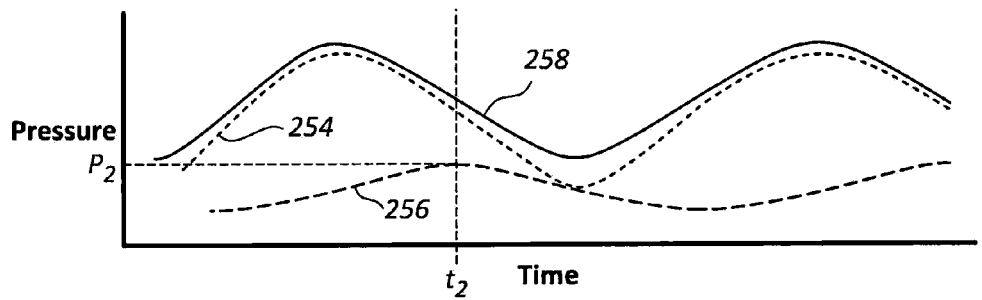
FIG. 12 is a graph showing a pressure waveform measured in a renal artery after ablation, decomposed into forward and reflected pressure waves.

FIG. 12 is a graph showing the forward and reflected pressure waves 254, 256 and pressure wave form 258 in the renal artery 92 after renal denervation. The pressure wave form 258 is generally lower than what is shown in FIG. 11 because the reflected pressure wave 256 is generally smaller as compared to the reflected pressure present prior to the renal denervation. Successful renal denervation typically provides a decrease in sympathetic tone of the renal artery 92 and other downstream vessels. The decrease in sympathetic tone may provide dilation of the vessels and a decrease in resistance to blood flow, which correlate with a reduced amplitude reflected pressure wave 256.

A comparison of the pressure wave form 258 prior to and after renal denervation may provide an indication of the efficacy of the renal denervation procedure. An operator may determine based on a change in the pressure wave form 258 or an absolute value of the pressure wave form 258 at various points in time (e.g., at the peaks of reflected pressure wave 256) whether the renal denervation procedure is sufficient. Upon successful renal denervation, arteries, arterioles and capillaries will undergo vasodilation, thus diminishing the amplitude and abruptness of the reflected wave 256.

A comparison of the graphs in FIGS. 10 and 11 shows that the reflected pressure wave 256 reaches a proximal site in the aorta at a time $t_1$, which is greater than the amount of time to reach a more distal side in the renal artery at a time $t_2$. A comparison of FIGS. 11 and 12 also shows that the reflected pressure wave 256 has a greater peak pressure $P_1$ prior to renal denervation than the peak pressure $P_2$ after the renal denervation. In some examples, the peak pressure values $P_1$, $P_2$ of the reflected pressure wave 256 for the times $t_1$, $t_2$ may be compared rather than comparing the pressure wave form 258 in order to determine the efficacy of the renal denervation procedure.

If the amplitude of the reflected pressure wave 256 drops by an absolute amount or a certain percentage of the initial amplitude $P_1$, renal denervation may be considered successful. Alternatively, the change may be quantified by assessing the morphology of the reflected wave using any non-morphology assessment method. In at least some examples, the pressure waveform and corresponding forward and reflected waves may be measured by a photoplethysmographic (PPG) sensor that calculates pressure using optical absorption at visible and near-infrared wavelengths or another pressure sensor.

Referring now to FIGS. 13-22, a further example system and related methods for renal denervation are disclosed. In this example, the renal denervation catheter includes at least two coils, spirals or loops (generally referred to as "coils" herein) positioned at spaced apart locations along the length of the catheter body. These coil features may be straightened or otherwise retained in a reduced profile shape during insertion of the catheter into the renal artery, and then may be deployed once the catheter is positioned within the renal artery. The proximal coil may be electrically charged to create an electromagnetic field, which aligns the dipoles of red blood cells (RBCs) within the blood flood B in the renal artery. Depending on the speed and turbulence of the blood flow B in a renal artery, some decay or randomness to the alignment of dipoles occurs. The net alignment of all the RBCs in the sample volume is detected as it passes through the distal coil by inducing a current that may be measurable. The amplitude of the measured current is adversely proportionate to the alignment of the RBC dipoles. Faster, and therefore more turbulent, renal artery blood flood B results in RBCs becoming less aligned and therefore capable of generating less current in the distal coil or loop. Since increases in renal blood flow may be considered a target of the renal denervation procedure, the absolute decrease or ratio metric decrease in current from pre-ablation to post-ablation may be used to determine the efficacy of the renal denervation procedure.

Figure 13:
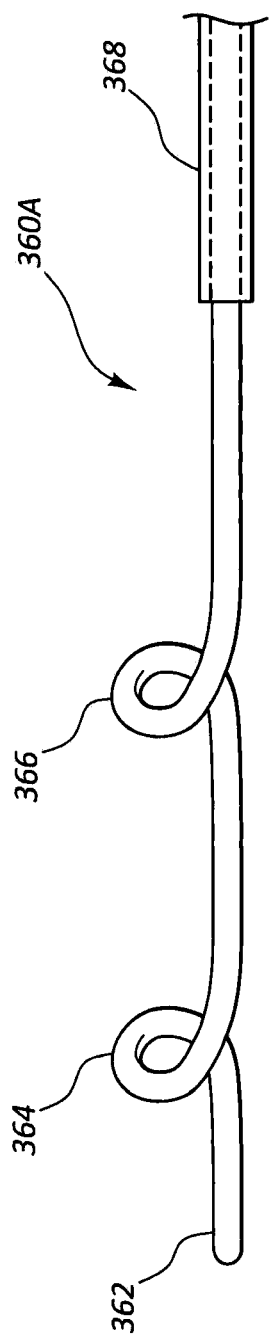
FIG. 13 shows an example blood alignment member in accordance with the present disclosure.
Figure 14:
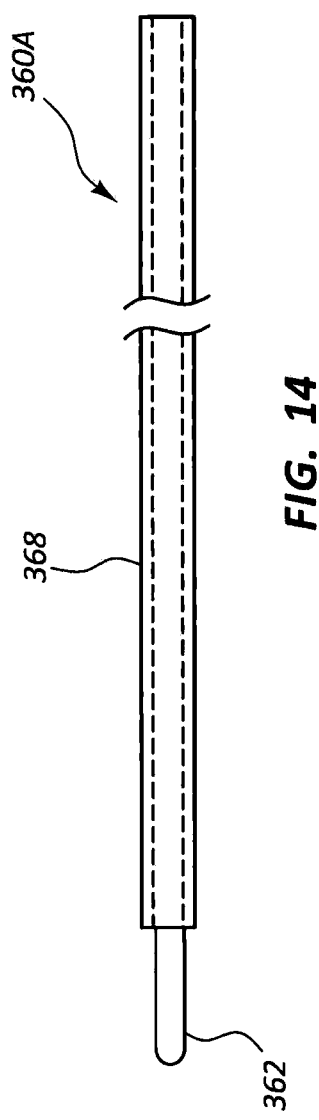
FIG. 14 shows the blood alignment member of FIG. 13 retained in a carrier tube.

FIGS. 13 and 14 show a blood alignment member 360A for use in a renal denervation procedure. The blood alignment member 360A may be referred to as a renal denervation catheter or a component of a renal denervation system. The blood alignment member 360A may include a distal tip 362, first and second loops 364, 366 (also referred to as coils—see FIG. 13), and a carrier tube 368 configured to hold the blood alignment member 360A in a straight, uncoiled orientation (i.e., without first and second loops 364, 366) during delivery into the renal artery. A controller or processor may be associated with the blood alignment member 360A.

Once the blood alignment member 360A is positioned within the renal artery, the carrier tube 368 may be withdrawn and the blood alignment member 360A may move into a coiled orientation to create the first and second loops 364, 366. In one example, the blood alignment member 360A includes a shape memory material such as, for example, Nitonol. In other examples, the blood alignment member 360A includes a temperature-activated material. In such an example, the blood alignment member 360A has a relatively straight orientation when in a cooled state (e.g., a temperature less than a threshold temperature), and moves into a pre-formed, shaped orientation after being heated above a threshold temperature. The heating of the blood alignment member 360A may result from heat transfer from the blood or vessel wall. The operator may have a certain amount of time (e.g., three to four minutes) to insert the blood alignment member 360A through the aorta and into the renal artery, whereupon the blood alignment member 360A is heated above the threshold temperature and automatically returned to an original form having the first and second loops 364, 366.

The second loop 366 may be configured to create an electromagnetic field within the renal artery. The second loop 366 may define an opening through which the blood flow B passes. The electromagnetic field may orient the dipoles of the RBCs in a certain direction (e.g., longitudinally). The blood flow B flows downstream and passed through an opening formed in the first loop 364. The first loop 364 may have a current induced therein upon passage of the oriented RBCs. The less oriented the RBCs are when passing through the first loop 364, the less current may be induced. Thus, the greater the velocity and turbulence of the blood flow B, the less current is induced in the first loop 364.

Referring to FIGS. 15-17, another example blood alignment member 360B is shown including first and second expandable coils 370, 372. The coils 370, 372 may be held in a restricted or contracted position using the carrier tube 368. Once the blood alignment member 360B is positioned within the renal artery, the carrier tube 368 may be withdrawn to expose the first and second expandable coils 370, 372 as shown in FIG. 16. The coils 370, 372 may expand automatically after withdrawing the carrier tube 368. Alternatively, the blood alignment member 360B may include other features (e.g., an expandable balloon) that expand the coils 370, 372 to an expanded or open position.

Once the first and second expandable coils 370, 372 are in an expanded position, an opening may be defined through the first and second expandable coils 370, 372 for passage of the blood flow B. The second coil 372 may be energized to create an electromagnetic field. Blood passing through the electromagnetic field may orient the dipoles of the RBCs in a predetermined orientation. The blood flow may pass through the first coil 370 and induce current therein due to the oriented RBCs. As described above, the more oriented the RBCs are in a common direction, the greater the current induced in first coil 370. The more turbulent the blood flow and the greater the velocity of the blood flow, the less the RBCs are oriented (e.g., are considered more random in their orientation) and thus less current is induced in first coil 370. A change in the amount of induced current in first coil 370 prior to and after the renal denervation procedure may help assess the efficacy of the renal denervation procedure.

The result of using the blood alignment members 360A, 360B in a renal artery 92 is shown schematically in FIG. 18. A plurality of randomly oriented blood cells $R_1$ in the blood flow B pass through the second loop 366. The second loop 366 may produce an electromagnetic field that orients the RBCs to form a plurality of oriented blood cell s $R_2$. Depending on the speed and turbulence of the blood flow B between loops 366 and 364, the RBCs may change into a more random orientation as shown in the blood cells $R_3$. The blood cells $R_3$ pass first through first loop 364 to induce a current in the first loop 364.

Figure 19:
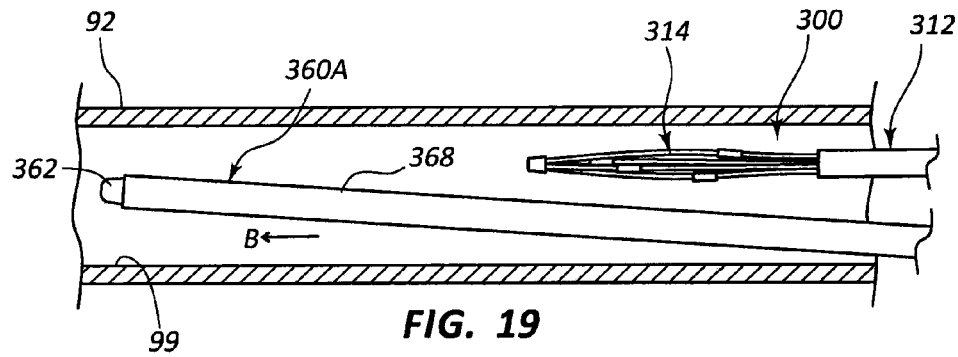
FIG. 19 shows the blood alignment member of FIG. 13 and a renal denervation catheter positioned in a vessel in a renal artery.
Figure 20:
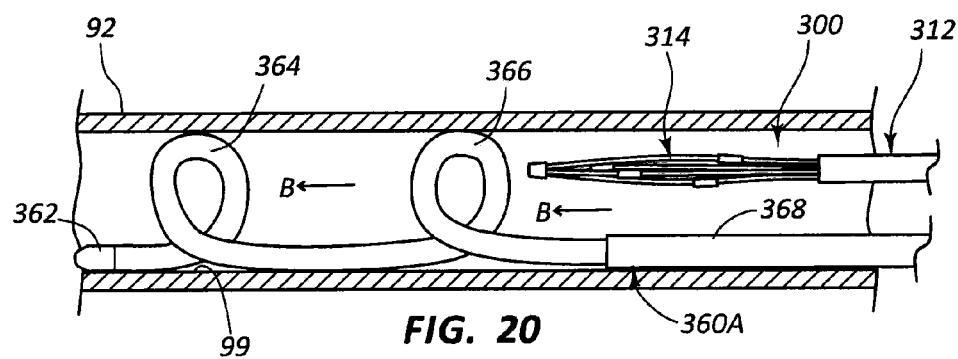
FIG. 20 shows the blood alignment member of FIG. 19 in a coiled position in the renal artery.

Referring now to FIGS. 19-22, an example method of renal denervation in assessing the efficacy of renal denervation is described. FIG. 19 shows the blood alignment member 360A positioned within a renal artery 92 downstream of a renal denervation catheter 300. The renal denervation catheter 300 may be operated to expand the deployable basket 314. The carrier tube 368 is withdrawn and the first and second loops 364, 366 are formed within the renal artery 92. Blood flow B passes through the second loop 366 to orient the RBCs, as shown in FIG. 20. The blood flow B passes through the first loop 364 to induce current in the first loop 364. The amount of induced current is measured and saved.

Figure 21:
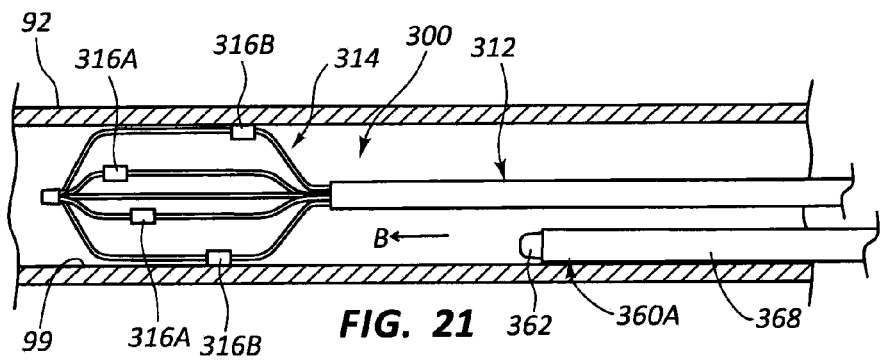
FIG. 21 shows the blood alignment member of FIG. 20 retracted into the carrier tube and the renal denervation catheter expanded to provide ablation of the renal artery.

Referring to FIG. 21, the carrier tube 368 is advanced to remove the first and second loops 364, 366, and the blood alignment member 360A is positioned proximal of the renal denervation catheter 300. The renal denervation catheter 300 is operated to expand the deployable basket 314 thereby positioning the ablation electrodes 316A,B in contact with an inner surface 99 of the renal artery 92. The ablation electrodes 316A,B are operated to ablate the renal artery 92 and associated renal nerves as part of a renal denervation procedure.

Figure 22:
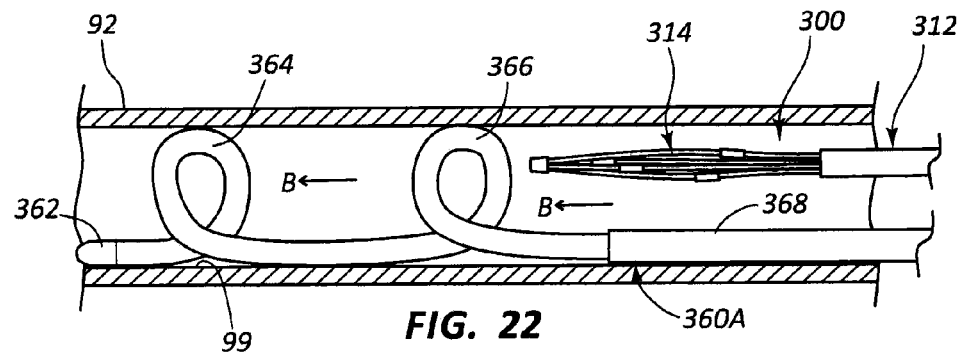
FIG. 22 shows the renal denervation catheter withdrawn and the blood alignment member in a coiled position.

FIG. 22 shows the deployable basket 314 contracted and the blood alignment member 360A positioned distal of the renal denervation catheter 300. The blood alignment member 360A is withdrawn and the first and second loops 364, 366 are formed within the renal artery 92. The blood flow B again passes through the second loop 366 to orient the RBCs, as shown in FIG. 22. The blood flow B then passes through the first loop 364 to generate a current in the first loop 364. The current is measured and compared to the current generated in first loop 364 prior to ablation in the steps discussed above with reference to FIG. 20. A change in induced current or an absolute value of the current induced post-ablation may be compared to threshold values. If the values meet the threshold values, the renal denervation resulting from ablation described with reference to FIG. 21 may be considered sufficient. If further ablation is needed, the step described with reference to FIG. 21 may be repeated as needed, followed by again measuring the induced current in first loop 364 as described with reference to FIG. 22. The induced current in any subsequent steps may be compared to any of the previously induced currents to help determine the efficacy of the renal denervation procedure.

Figure 23:
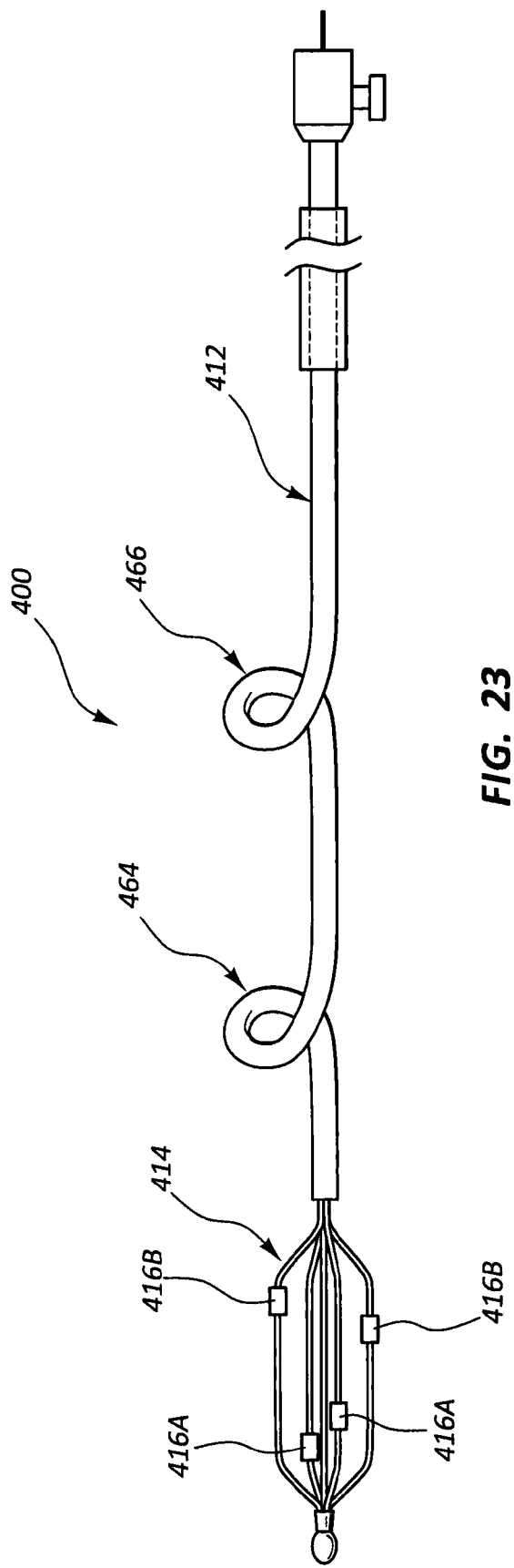
FIG. 23 shows an integrated renal denervation catheter and blood alignment member in accordance with the present disclosure.

While the renal denervation system described with reference to FIGS. 15-22 includes a separate blood alignment member and a renal denervation catheter, other embodiments are possible in which the renal denervation catheter includes features of the blood alignment member. For example, the first and second loops 364, 366 may be formed in the catheter shaft 312 proximal of the deployable basket 314. In another example, the first and second expandable coils 370, 372 may be carried by the catheter shaft 312 at a location proximal of the deployable basket 314. FIG. 23 shows an example renal denervation catheter having features of the blood alignment member 360A.

The renal denervation catheter 400 shown in FIG. 23 includes a catheter shaft 412 having first and second loops 464, 466 formed therein, and a deployable basket 414 carrying a plurality of ablation electrodes 416A,B. The first and second loops 464, 466 may remain positioned in the renal artery 92 prior to, during and after operating the ablation members carried by the deployable basket 414 to provide renal denervation. A controller or processor (e.g., controller 20 described above) may be used with the renal denervation catheter 400.

The various systems and methods disclosed herein may provide feedback during a renal denervation procedure to help minimize the number of ablation sites, time and energy required for each ablation. The systems and methods may determine a change in blood flow rate using injection of contrast in renal arteries to determine efficacy of the ablation. An impedance measurement in a renal artery may provide indication of the degree of vessel distention. Decomposition of a pressure wave form into forward and reflected waves prior to and after renal denervation may be used to determine efficacy of the renal denervation procedure. The catheter designs in accordance with the present disclosure may allow for blood flow through the catheter while maintaining contact with the vessel wall, and characteristics of the blood flow may be used to help determine efficacy of the renal denervation. The devices and methods disclosed herein may provide alignment of RBCs as an indicator of turbulence in the blood flow, and thus changes in blood flow correlating to the efficacy of the renal denervation procedure.

As used in this specification and the appended claims, the terms "engage" and "engagable" are used broadly to mean interlock, mesh, or contact between two structures or devices. A "tube" is an elongated device with a passageway. A "lumen" refers to any open space or cavity in a bodily organ, especially in a blood vessel. The words "including" and "having," as well as their derivatives, as used in the specification, including the claims, have the same meaning as the word "comprising."

The preceding description has been presented only to illustrate and describe exemplary embodiments of the invention. It is not intended to be exhaustive or to limit the invention to any precise form disclosed. Many modifications and variations are possible in light of the above teaching. It is intended that the scope of the invention be defined by the following claims.

What is claimed is:

1. A renal denervation system, comprising:
 a renal denervation catheter having a plurality of ablation members positioned at a distal end portion thereof and being insertable into a renal artery;
 a flow determining system selected from the group consisting of:
  a first flow determining member comprising at least one fluid port configured to release a flow of fluid into the renal artery, a second flow determining member comprising at least one sensor configured to detect the flow of the fluid, and a processor configured to determine a time delay between releasing the flow of fluid and detecting the flow of fluid prior to and after treating the renal artery with the renal denervation catheter;
  a first flow determining member and a second flow determining member being spaced apart along a length of the renal denervation catheter each comprising at least one pressure sensor configured to measure a pressure wave advanced through the renal artery in a first direction and reflected through the renal artery in an opposite direction, and a processor configured to determine a change in amplitude of the pressure wave reflected through the renal artery; and
  a first flow determining member and a second flow determining member each comprising at least one wire coil, the first flow determining member configured to generate an electromagnetic field to orient dipoles of red blood cells in the blood flow passing through the at least one wire coil of the first flow determining member, the red blood cells inducing current in the at least one wire coil of the second flow determining member, and a processor configured to determine a change in blood flow through the renal artery resulting from a renal denervation procedure using the renal denervation catheter and in response to input from the first and second flow determining members.

2. The renal denervation system of claim 1, wherein a difference in the time delay prior to and after treating the renal artery with the renal denervation catheter corresponds to a change in blood flow.

3. The renal denervation system of claim 1, wherein the renal denervation catheter comprises a basket construction having a plurality of arms, and the plurality of ablation members are positioned on separate ones of the plurality of arms.

4. The renal denervation system of claim 1, wherein the renal denervation catheter operates using one of radiofrequency and ultrasound.

5. A method of determining efficacy of a renal denervation procedure in a renal artery, comprising:
 providing a renal denervation catheter and a flow determining system;
 determining a preliminary flow characteristic of blood flow through the renal artery;
 ablating the renal artery with the renal denervation catheter as part of a renal denervation procedure;
 determining a subsequent flow characteristic of blood flow through the renal artery after ablating;
 comparing the preliminary flow characteristic with the subsequent flow characteristic to determine a change in blood flow, which corresponds to efficacy of the renal denervation procedure,
 wherein determining the preliminary and subsequent flow characteristic comprises at least one of:

injecting a flow of fluid into the blood flow at a first location and determining a presence of the flow of fluid at an axially spaced apart second location;

sensing with the flow determining system a pressure wave in the blood flow in a first direction and in an opposite direction by determining an amplitude of the pressure wave; and generating an electromagnetic field that orients dipoles of red blood cells in the blood flow passing through a first coil of the flow determining system, the red blood cells inducing a current in a second coil of the flow determining system upon passing through the second coil downstream of the first coil.

6. A method of determining blood flow in a renal artery during a renal denervation procedure, the method comprising:

performing renal denervation on the renal artery;

determining a blood flow characteristic prior to and after performing renal denervation;

comparing the blood flow characteristic determined prior to and after performing renal denervation to determine whether blood flow has increased above a threshold level, wherein determining the blood flow characteristic comprises at least one of:

injecting a flow of fluid into the renal artery at a first location and determining a presence of the flow of fluid at a second location downstream of the first location;

sensing an amplitude of a pressure wave in the blood flow in a first direction and in an opposite second direction; and orienting dipoles of red blood cells in the blood flow at a first location, and passing the red blood cells through a coil at a downstream location to induce a current.

* * * * *